US009220620B2

(12) United States Patent
Hadley et al.

(10) Patent No.: US 9,220,620 B2
(45) Date of Patent: Dec. 29, 2015

(54) ENDOLUMINAL PROSTHESIS INTRODUCER

(71) Applicant: Cook Medical Technologies LLC, Bloomington, IN (US)

(72) Inventors: Rick Hadley, Otterbein, IN (US); William J. Havel, Lafayette, IN (US); Jeffry S. Melsheimer, Springville, IN (US); Matthew S. Huser, West Lafayette, IN (US); William K. Dierking, Louisville, KY (US); Per Hendriksen, Herlufmagle (DK); Siddharth Vad, Bloomington, IN (US); Michael P. DeBruyne, Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 189 days.

(21) Appl. No.: 13/669,145

(22) Filed: Nov. 5, 2012

(65) Prior Publication Data
US 2013/0131775 A1    May 23, 2013

Related U.S. Application Data

(60) Provisional application No. 61/562,641, filed on Nov. 22, 2011.

(51) Int. Cl.
*A61F 2/06* (2013.01)
*A61F 2/966* (2013.01)
(Continued)

(52) U.S. Cl.
CPC . *A61F 2/966* (2013.01); *A61F 2/07* (2013.01); *A61F 2002/8486* (2013.01); *A61F 2002/9534* (2013.01); *A61F 2002/9665* (2013.01)

(58) Field of Classification Search
CPC ............ A61F 2/966; A61F 2002/8486; A61F 2002/9534; A61F 2002/9665; A61F 2/07

USPC ......................................................... 623/1.11
See application file for complete search history.

(56) References Cited

U.S. PATENT DOCUMENTS

| 5,562,726 A | 10/1996 | Chuter ............................ 623/1 |
| 6,391,050 B1 | 5/2002 | Broome ....................... 623/1.11 |

(Continued)

FOREIGN PATENT DOCUMENTS

| EP | 1 369 098 A1 | 10/2003 |
| EP | 1 400 219 A1 | 3/2004 |

(Continued)

OTHER PUBLICATIONS

Extended European Search Report for EP 12275180.3, dated Feb. 15, 2013, pp. 1-9, European Patent Office, Rijswijk, The Netherlands.

*Primary Examiner* — Katherine M Shi
*Assistant Examiner* — Mohamed Gabr
(74) *Attorney, Agent, or Firm* — Brinks Gilson & Lione

(57) ABSTRACT

An endoluminal prosthesis introducer may include a rotatable inner cannula including a proximal end. The introducer may include a proximal tip disposed at the proximal end of the inner cannula and including a distal end. The introducer may include a retaining member including an engaging member extending radially outward. The retaining member may be disposed about the proximal end of the inner cannula. In response to rotation of the inner cannula with respect to the retaining member, the proximal tip may be longitudinally movable relative to the engaging member between a retaining configuration and a releasing configuration. The proximal tip and the engaging member may be spaced from one another by a greater longitudinal distance in the releasing configuration than in the retaining configuration.

19 Claims, 17 Drawing Sheets

(51) Int. Cl.
  *A61F 2/07*    (2013.01)
  *A61F 2/848*   (2013.01)
  *A61F 2/95*    (2013.01)

(56) References Cited

U.S. PATENT DOCUMENTS

| | | | |
|---|---|---|---|
| 6,790,221 B2 * | 9/2004 | Monroe et al. | 623/1.11 |
| 6,858,034 B1 | 2/2005 | Hijlkema et al. | 606/108 |
| 6,939,370 B2 | 9/2005 | Hartley et al. | 623/1.11 |
| 7,264,632 B2 * | 9/2007 | Wright et al. | 623/1.12 |
| 7,435,253 B1 | 10/2008 | Hartley et al. | 623/1.12 |
| 7,763,063 B2 | 7/2010 | Arbefeuille et al. | 623/1.11 |
| 7,763,066 B2 | 7/2010 | Parker | 623/1.15 |
| 7,771,463 B2 | 8/2010 | Ton et al. | 623/1.11 |
| 7,918,880 B2 | 4/2011 | Austin | 623/1.11 |
| 8,070,790 B2 | 12/2011 | Berra et al. | 623/1.12 |
| 2003/0074057 A1 | 4/2003 | Rosengart | 623/1.23 |
| 2004/0260377 A1 | 12/2004 | Flomenblit et al. | 623/1.11 |
| 2005/0049667 A1 | 3/2005 | Arbefeuille et al. | 623/1.11 |
| 2005/0288766 A1 | 12/2005 | Plain et al. | 623/1.12 |
| 2006/0004433 A1 | 1/2006 | Greenberg et al. | 623/1.11 |
| 2006/0058864 A1 | 3/2006 | Schaeffer et al. | 623/1.11 |
| 2006/0136035 A1 | 6/2006 | Hermann et al. | 623/1.11 |
| 2006/0276872 A1 * | 12/2006 | Arbefeuille et al. | 623/1.11 |
| 2007/0043419 A1 | 2/2007 | Nikolchev et al. | 623/1.11 |
| 2010/0298931 A1 | 11/2010 | Quadri et al. | 623/2.11 |
| 2011/0137401 A1 | 6/2011 | Dorn et al. | 623/1.12 |
| 2011/0144735 A1 | 6/2011 | Hartley et al. | 623/1.11 |
| 2011/0178588 A1 | 7/2011 | Haselby | 623/1.11 |
| 2011/0251667 A1 | 10/2011 | Argentine | 623/1.11 |
| 2011/0257720 A1 | 10/2011 | Peterson et al. | 623/1.11 |

FOREIGN PATENT DOCUMENTS

| | | |
|---|---|---|
| EP | 1 982 677 A2 | 10/2008 |
| WO | WO 2009/121006 A1 | 1/2009 |

* cited by examiner

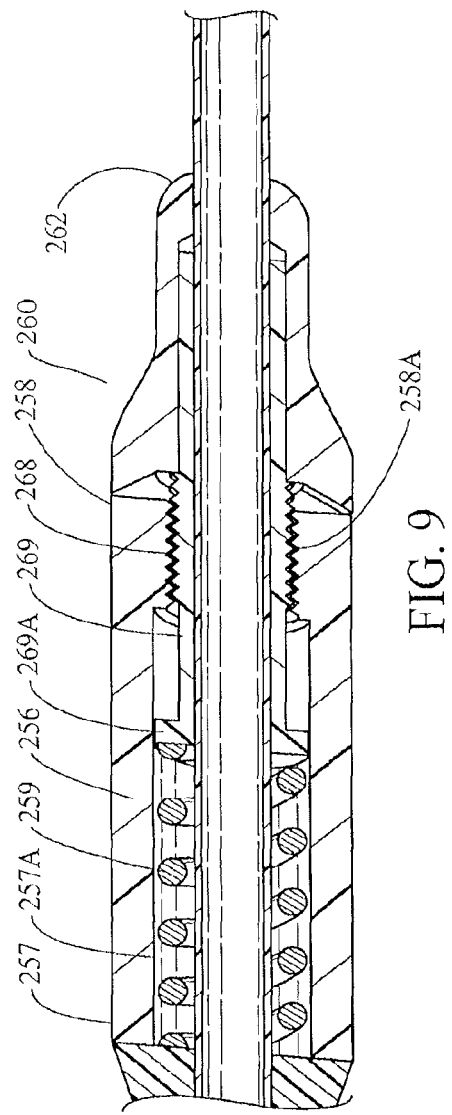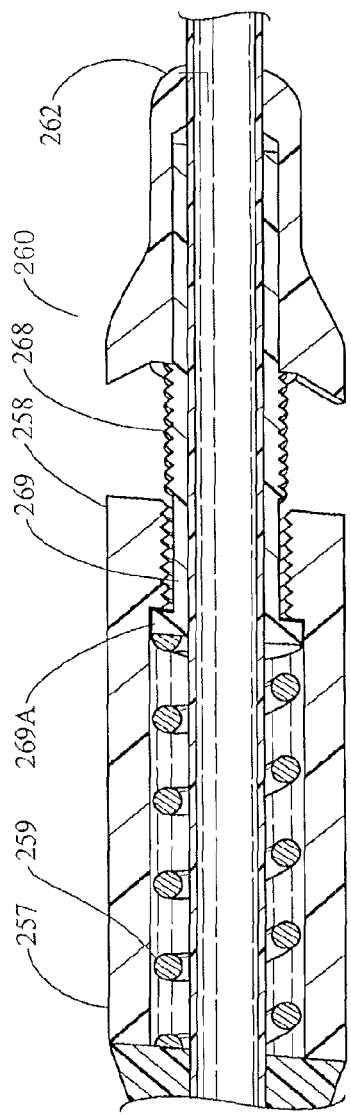
FIG. 9
FIG. 10

ENDOLUMINAL PROSTHESIS INTRODUCER

CROSS-REFERENCE TO RELATED APPLICATIONS

This application claims priority and the benefit of provisional U.S. Patent Application Ser. No. 61/562,641, filed Nov. 22, 2011, which is incorporated herein by reference in its entirety.

TECHNICAL FIELD

This disclosure relates to medical devices and more particularly to an introducer for introducing a prosthesis into a human or animal body.

BACKGROUND

In the deployment of a prosthesis such as a stent or stent graft into the human or animal body via intraluminal techniques, an introducer or delivery device is used to introduce the prosthesis into a vessel or a lumen of the body. After the prosthesis has been deployed and expanded within the lumen, the introducer is withdrawn from the body.

Stents may be inserted into an anatomical vessel or duct for various purposes. Stents may maintain or restore patency in a formerly blocked or constricted passageway, for example, following a balloon angioplasty procedure. Other stents may be used for different procedures. For example, stents placed in or about a graft have been used to hold the graft in an open configuration to treat an aneurysm. Additionally, stents coupled to one or both ends of a graft may extend proximally or distally away from the graft to engage a healthy portion of a vessel wall away from a diseased portion of an aneurysm to provide endovascular graft fixation.

Stents may be either self-expanding or balloon-expandable, or they may have characteristics of both types of stents. Self-expanding stents may be delivered to a target site in a compressed configuration and subsequently expanded by removing a delivery sheath, removing trigger wires, and/or releasing diameter reducing ties. With self-expanding stents, the stents expand primarily based on their own expansive force without the need for further mechanical expansion. In a stent made of a shape memory alloy such as nitinol, the shape memory alloy may be employed to cause the stent to return to a predetermined configuration upon removal of the sheath or other device maintaining the stent in its pre-deployment configuration.

When trigger wires are used as a deployment control mechanism, the trigger wires may releasably couple the proximal and/or distal ends of a stent or stent graft to a delivery catheter. Typically, one or more trigger wires are looped through a portion of the stent near a vertex of the stent. For example, trigger wires may be used to restrain a Z-stent or Gianturco stent formed of a series of substantially straight segments interconnected by a series of bent segments. The trigger wires may be disposed through, and pull upon, the bent segments to pull the stent closely against the delivery catheter. Trigger wires also may be used in conjunction with different stent designs such as cannula-cut stents having acute or pointed bends. In such examples, the trigger wires may be looped around one or more vertices formed beneath the proximal and/or distal apices, for example, at a location where an individual apex splits into two separate strut segments. Any of the stents may have barbs and/or other anchoring members to help decrease prosthesis migration.

One form of introducer uses a proximal nose cone with a distally facing capsule to encompass an exposed stent and barbs on the exposed stent of a stent graft during introduction. After the stent graft has been released and the capsule has been removed from the exposed stent, the capsule, along with the introducer, is withdrawn from the body. The capsule, however, has a distally facing opening with a surrounding edge. This edge may engage with stents of the just introduced stent graft and dislodge the stent graft from its position on the wall of the body vessel. Similarly, the sheath of the introducer generally has a proximally facing opening and a surrounding edge. If the sheath is advanced to meet the distally facing capsule, the edge of the sheath may engage with stents of the just introduced stent graft and dislodge the stent graft from its position on the wall of the body vessel. It is desirable to engage the sheath with the capsule before withdrawal. Therefore, it also is desirable to prevent the edges of the capsule and the sheath from dislodging the stent graft when the sheath and the capsule are brought into engagement.

Additionally, operation of the introducer may require manipulation of multiple trigger wires in a specified order. This may add to the complexity of the introducer. Such trigger wires also may add to the overall diameter or profile of the introducer. It is desirable, therefore, to reduce the number of trigger wires required to operate an introducer.

SUMMARY

The present embodiments provide an introducer for intraluminal deployment of a stent or stent graft.

In one example, an endoluminal prosthesis introducer may include a rotatable inner cannula including a proximal end. The introducer may include a proximal tip disposed at the proximal end of the inner cannula and including a distal end. The introducer may include a retaining member including an engaging member extending radially outward. The retaining member may be disposed about the proximal end of the inner cannula. In response to rotation of the inner cannula with respect to the retaining member, the proximal tip may be longitudinally movable relative to the engaging member between a retaining configuration and a releasing configuration. The proximal tip and the engaging member may be spaced from one another by a greater longitudinal distance in the releasing configuration than in the retaining configuration.

In another example, a system may include an introducer and an endoluminal prosthesis loaded on the introducer. The prosthesis may include a stent end engaged by the introducer and retained in a compressed configuration. The introducer may include a rotatable inner cannula including a proximal end. The introducer may include a proximal tip disposed at the proximal end of the inner cannula and including a distal end. The introducer may include a retaining member disposed about the proximal end of the inner cannula and including a sleeve and an engaging member extending radially from the sleeve and engaged with the stent end in the compressed configuration. The stent end may be retained against the distal end of the proximal tip. In response to rotation of the inner cannula with respect to the prosthesis and the retaining member, the proximal tip may be longitudinally movable relative to the engaging member from a retaining configuration to a releasing configuration, and the stent end may be releasable from engagement with the engaging member.

In another example, a method for deploying an endoluminal prosthesis within a body vessel may include introducing the prosthesis into the body vessel with an introducer. The introducer may include an inner cannula, a proximal tip disposed at a proximal end of the inner cannula, and a retaining member disposed about the proximal end of the inner cannula and engaged with a stent end of the prosthesis. The stent end may be captured between the retaining member and a distal end of the proximal tip and retained in a compressed configuration. The method may include moving the proximal tip proximally relative to the retaining member by rotating the inner cannula relative to the retaining member.

Other systems, methods, features, and advantages of the invention will be, or will become, apparent to one with skill in the art upon examination of the following figures and detailed description. It is intended that all such additional systems, methods, features, and advantages be within the scope of the invention, and be encompassed by the following claims.

BRIEF DESCRIPTIONS OF THE DRAWINGS

FIGS. 9-10 are longitudinal cross sectional views of a proximal portion of another example of an introducer having a stent retaining member.

DETAILED DESCRIPTION OF THE DRAWINGS AND THE PRESENTLY PREFERRED EMBODIMENTS

The present disclosure relates to an introducer for intraluminal deployment of a prosthesis such as a stent or stent graft and methods for deploying such a prosthesis. The embodiments described in this disclosure will be discussed generally in relation to deployment of stent grafts into the aorta, but the disclosure is not so limited and can be applied to other vasculature or other body vessels or lumens.

In the present disclosure, the term "proximal" refers to a direction that is generally closest to the heart during a medical procedure, while the term "distal" refers to a direction that is farthest from the heart during a medical procedure.

The term "stent graft" refers to a device which has a tubular body of biocompatible graft material and at least one stent fastened to the tubular body to define a lumen through the stent graft. The stent graft may be bifurcated and/or may include fenestrations, side arms, or the like. Other arrangements of stent grafts also are within the scope of this disclosure.

Figure 1:
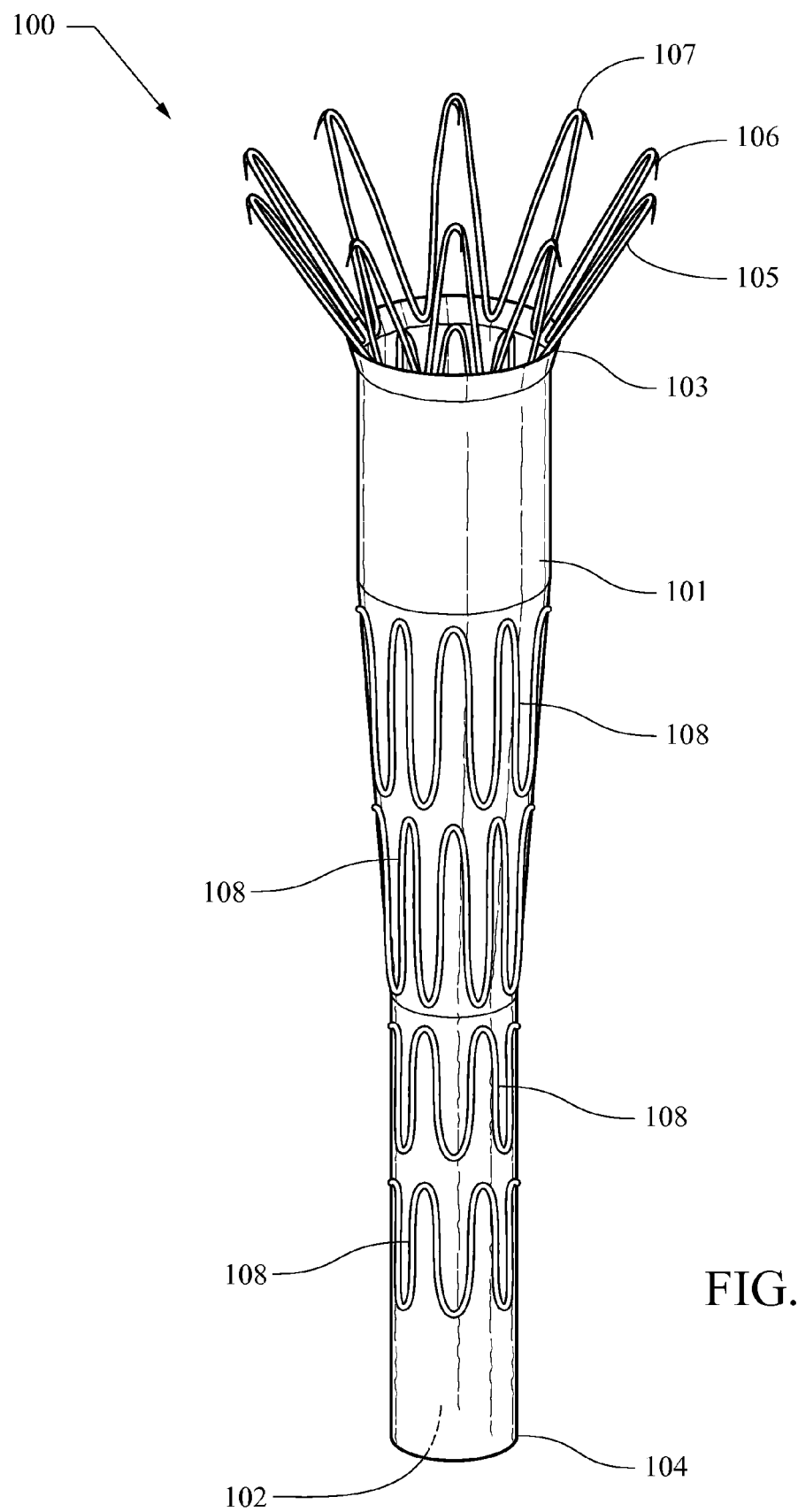
FIG. 1 illustrates one example of a stent graft.

FIG. 1 depicts one embodiment of a stent graft 100 that may be deployed using an introducer or delivery device as further described below. The stent graft 100 may be of a self expanding type having resilient stents to enable the stent graft to expand upon release from the introducer. The stent graft 100 may include a graft body 101 having a generally tapering tubular configuration. In other examples, the graft body 101 may have a generally cylindrical tubular configuration with a substantially constant diameter. The graft body 101 may have a lumen 102 extending longitudinally between a proximal end 103 and a distal end 104 thereof. An attachment stent 105 may extend proximally beyond the proximal end 103 of the graft body 101. Additional stents 108 may be positioned along the length of the graft body 101.

The stent 105 may include distally extending projections 106. The projections 106 may be disposed generally internal or external to the lumen 102 of the stent graft 100. In one example, the projections 106 may be disposed substantially external to the lumen 102 of the stent graft 100 when the stent graft is deployed. The projections 106 may be configured as barbs as shown in FIG. 1. Such barbs may be configured to engage a wall of a body vessel upon deployment of the stent graft from the introducer to fix the stent graft in place relative to the body vessel. Alternatively, the projections 106 may be configured as tabs or any other form of projecting member. Such tabs may be disposed generally internal to the lumen 102 of the stent graft 100 or external to the lumen of the stent graft. In one example, the tabs may be disposed generally along a surface plane of the stent graft 100 upon deployment of the stent graft from the introducer. Such tabs may lie substantially flat against the attachment stent and/or the graft body when the stent graft is deployed. In other words, such tabs may not extend outward from the stent graft to engage the wall of the body vessel upon deployment of the stent graft. The projections 106 may extend from a proximal end 107 of the stent graft 100. The proximal end 107 may be defined by a plurality of bends of the stent 105. If the projections 106 are disposed external to the lumen 102 of the stent graft 100, the projections may be everted to a position generally within the lumen 102 for engagement with a deployment member of the introducer as further described below.

Figure 2:
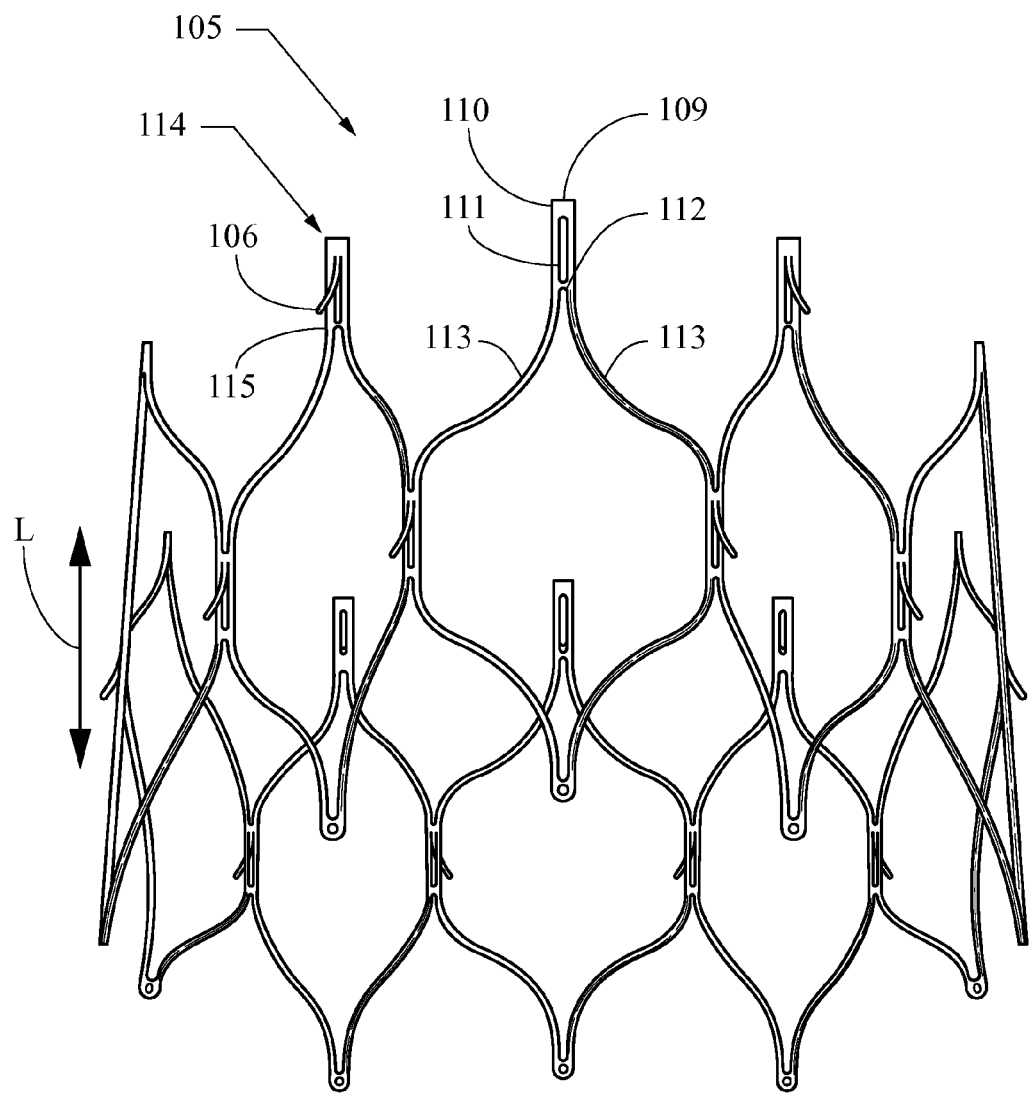
FIG. 2 illustrates one example of an attachment stent.

In one example, the attachment stent 105 may be configured as shown in FIG. 2 and described in U.S. Patent Application Pub. No. 2009/0204202 by Dierking et al., which is incorporated by reference herein in its entirety. For example, the attachment stent 105 may include one or more first proximal apices 109. Each first proximal apex 109 may include an end region 110 having an aperture 111 formed therein. The aperture 111 may be configured to receive a stent engaging member of an introducer as further described below. The end region 110 may be positioned proximal of the bend 112 between two adjacent struts 113 of the stent 105. In other words, the end region 110 may be configured as an eyelet extending proximally from the bend 112 between two adjacent struts 113 to receive the stent engaging member of the introducer. Upon compression of the stent 105, the stent engaging member may not be pinched between the adjacent struts of the stent. In other words, the eyelet may remain open even after compression of the stent 105. This may avoid damage to the struts 113 which may be caused by pinching the stent engaging member between the struts.

Additionally, or alternatively, the attachment stent 105 may include one or more second proximal apices 114. Each second proximal apex 114 may include an end region 115 having an integral barb 106 formed therein. The barb 106 may be configured to engage a wall of a body vessel to prevent migration of the stent graft 100 within the body vessel. The stent 105 may include alternating first proximal apices and second proximal apices, as shown in FIG. 2, so that every other apex may be engaged by a stent engaging member. In other examples, the stent 105 may have any number of first proximal apices and second proximal apices. In one example, each apex of the attachment stent 105 may be configured as a first proximal apex (i.e., each apex may include an end region 110 with an aperture 111). In this manner, each apex of the stent 105 may be engaged by a stent engaging member of the introducer.

Although the operation of the introducer will be described with reference to the stent graft 100, a person having ordinary skill in the art will recognize that the introducer may be used with a stent or stent graft having any other configuration. For example, the introducer described below may be used for intraluminal deployment of a bifurcated stent graft, a stent graft having one or more branches, scallops, and/or fenestrations, or any other type of stent graft. Additionally, or alternatively, the introducer may be used for intraluminal deployment of a bare stent or any other type of prosthesis including, for example, a self-expanding stent. Such embodiments are contemplated by and within the scope of this disclosure.

Figure 3:
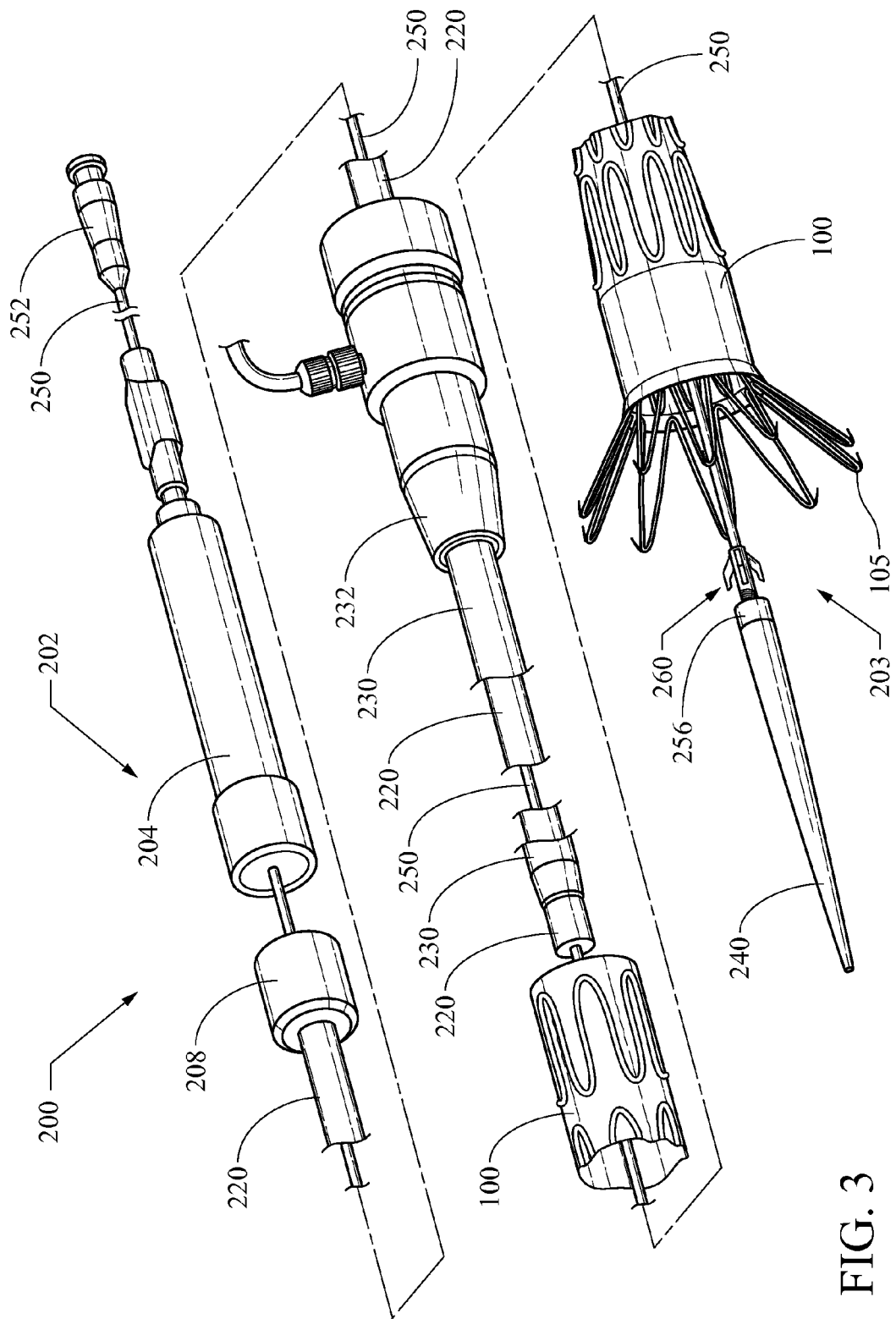
FIG. 3 illustrates one example of an introducer.

FIG. 3 illustrates one example of an introducer 200, which may be used to deliver and deploy a prosthesis (e.g., the stent graft 100) as further described below. The introducer 200 may include a handle portion 202 and an introduction portion 203. The handle portion 202 may remain outside of the patient in use, and the introduction portion 203 may be introduced into the patient via a puncture in an artery such as a femoral artery. The introducer 200 may include a catheter, such as the pusher catheter 220. The pusher catheter 220 may extend proximally from the handle 202. The pusher catheter 220 may be configured as an elongate tubular member having a lumen extending longitudinally therein.

The introducer 200 may include a sheath 230 and a sheath hub 232 extending over at least a portion of the pusher catheter 220. The sheath 230 may be configured as an elongate tubular member having a lumen extending longitudinally therein. The pusher catheter 220 may be slidably received within the lumen of the sheath 230. The sheath 230 may extend proximally from the sheath hub 232 to a proximal tip 240 of the introducer 200 for delivery of the prosthesis. The sheath 230 may be retracted relative to the pusher catheter 220 to at least partially expose the prosthesis retained below the sheath and positioned at a prosthesis retention section near the proximal end of the introducer 200 as further described below.

The introducer 200 may include an inner cannula 250. The inner cannula 250 may extend from a connector 252 (e.g., a Luer lock hub) positioned at the distal end of the introducer 200, through the handle 202 and the pusher catheter 220, and to the proximal tip 240. The inner cannula 250 may be configured as an elongate tubular member having a lumen extending longitudinally therein. The inner cannula 250 may be received within the lumen of the pusher catheter 220. The inner cannula 250 may extend at least partially through the proximal tip 240. The inner cannula 250 may be tracked over a guide wire in a conventional manner to guide the introducer 200 through the vasculature of the patient. The connector 252 may be used to introduce liquids such as contrast media to enable tracking of the progress of an operation.

In one example, the handle 202 may include a cannula handle 204 and a pusher handle 208 as shown in FIG. 3. The cannula handle 204 may be coupled to the inner cannula 250. Additionally, or alternatively, the pusher handle 208 may be coupled to the pusher catheter 220. The cannula handle 204 may be rotatable and/or translatable relative to the pusher handle 208. The inner cannula 250 may be rotated and/or translated relative to the pusher catheter 220 (e.g., by rotation and/or translation of the cannula handle relative to the pusher handle). The cannula handle 204 may be rotated (e.g., relative to the pusher handle 208) to rotate the inner cannula 250 for releasing a prosthesis as further described below. Rotation and/or translation of the cannula handle 204 relative to the pusher handle 208 may be inhibited by any suitable means. For example, the handle 200 may include a locking mechanism (e.g., as described below with reference to FIG. 13) to inhibit rotation and/or translation of the cannula handle 204 relative to the pusher handle 208.

In another example, the handle 202 may be configured as a unitary handle coupled to the inner cannula 250 and/or the pusher catheter 220. The inner cannula 250 and the pusher catheter 220 may be rotated together (e.g., by rotation of the handle 202) to rotate the inner cannula for releasing the prosthesis. Alternatively, the inner cannula 250 may be rotated relative to the handle 202 and/or the pusher catheter 220 for releasing the prosthesis.

Figure 4:
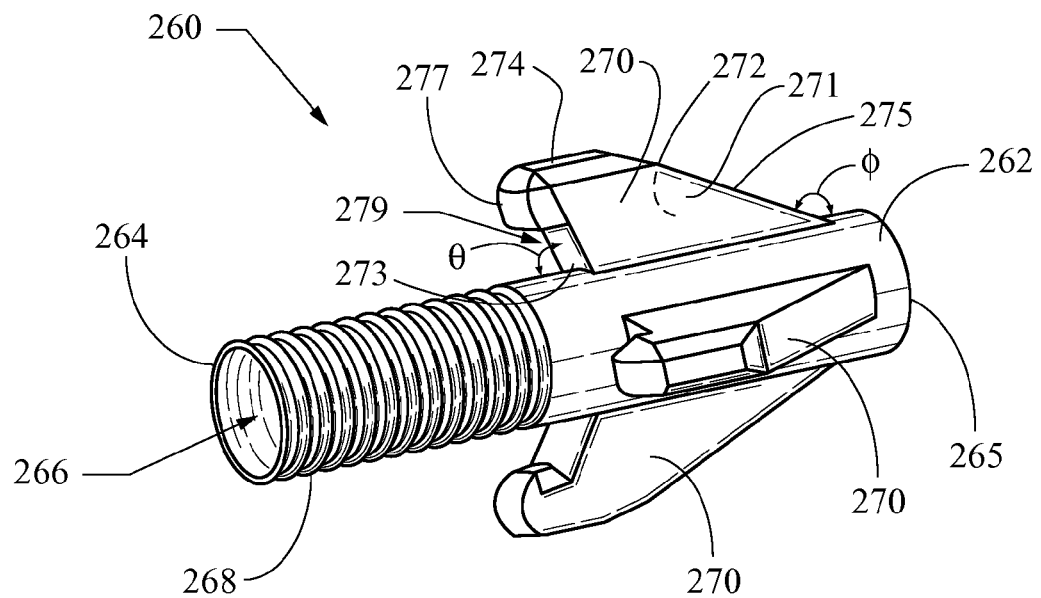
FIG. 4 illustrates the stent retaining member of the introducer of FIG. 3.

The introducer 200 may include a retaining member such as a stent retaining member 260 positioned at the prosthesis retention section. FIG. 4 illustrates one example of the stent retaining member 260. The stent retaining member 260 may include a sleeve 262 extending over at least a portion of the inner cannula 250. The sleeve 262 may be configured as a tubular member having a proximal end 264, a distal end 265, and a lumen 266 extending longitudinally within the sleeve. The inner cannula 250 may be received within the lumen 266 of the sleeve 262. The inner cannula 250 and the stent retaining member 260 may be rotatable and/or translatable relative to one another to deploy the prosthesis as further described below. The sleeve 262 may include an attachment mechanism such as a threaded segment 268 positioned at the proximal end 264 as shown in FIG. 4. The threaded segment 268 may include external threads positioned on the outer surface of the sleeve 262. The threaded segment 268 may engage the inner cannula 250 and/or the proximal tip 240 of the introducer 200 to releasably couple the stent retaining member 260 to the inner cannula as further described below. In other examples, the sleeve 262 may include any other type of attachment mechanism capable of releasably attaching the sleeve to the proximal tip as further described below.

In one example, the sleeve 262 may be configured as a torque shaft segment. To that end, the distal end 265 of the sleeve 262 may be positioned at the introduction portion (e.g., at the prosthesis retention section) near the proximal end of the introducer 200. Additionally, or alternatively, the distal end 265 of the sleeve may be positioned proximal of the proximal end of the pusher catheter 220 (e.g., between the pusher catheter and the distal end of the proximal tip 240) and/or proximal of the handle 202. The sleeve may be unattached to the handle 202 of the introducer 200.

The stent retaining member 260 may include one or more engaging members such as one or more stent engaging members 270 extending radially from the sleeve 262. The stent engaging members 270 may be configured to engage a portion of the prosthesis to retain the engaged portion of the prosthesis in a compressed configuration. For example, each stent engaging member 270 may engage an apex of a stent (e.g., the stent 105 of the stent graft 100) as further described below. The stent engaging members 270 may be spaced from one another about the circumference of the sleeve 262. In one example, the stent retaining member 260 may include four stent engaging members 270 positioned approximately 90 degrees from one another about the circumference of the sleeve 262 as shown in FIG. 4. In other examples, the stent retaining member may include any number of stent engaging members spaced at any distance from one another about the circumference of the sleeve 262. In one example, the number of stent engaging members may be equal to one-half of the number of apices of the stent 105 of the stent graft 100. In this manner, the stent retaining member may be configured to engage every other apex of the stent 105 to retain the stent 105 in a partially expanded configuration as further described below. Alternatively, the number of stent engaging members may be equal to the number of apices of the stent 105. In this manner, the stent retaining member may be configured to engage every apex of the stent 105 to retain the stent 105 in the partially expanded configuration as further described below. In other examples, the stent retaining member may include any number of stent engaging members to engage any portion of a prosthesis.

Each stent engaging member 270 may be configured as a fin or rib extending longitudinally along the sleeve 262 and laterally or radially away from the sleeve as shown in FIG. 4. The stent engaging member 270 may be positioned longitudinally between the threaded segment 268 and the distal end 265 of the sleeve 262. Additionally, or alternatively, the distal end of the stent engaging member 270 may be substantially longitudinally aligned with the distal end of the sleeve. The stent engaging member 270 may include a relatively thin body having a first surface 271 and a second surface 272 positioned opposite the first surface. Each of the first surface 271 and the second surface 272 may extend along the length of the sleeve 262 and outward away from the sleeve. Each of the first surface 271 and the second surface 272 may be configured as a substantially planar surface. The first surface 271 and the second surface 272 may be substantially parallel to one another such that the thickness of the stent engaging member 270 is substantially constant along the length and the height of the stent engaging member. Alternatively, the first surface 271 and the second surface 272 may be non-parallel to one another such that the thickness of the stent engaging member 270 varies along the length and/or the height of the stent engaging member. In other examples, the first surface 271 and/or the second surface 272 may be non-planar. For example, the first surface 271 and/or the second surface 272 may be curved toward one another such that the thickness of the stent engaging member decreases in a radially outward direction.

The stent engaging member 270 may include a proximal edge 273, an outer edge 274, and a distal edge 275 as shown in FIG. 4. The proximal edge 273 and the distal edge 275 may be joined to one another by the outer edge 274. The proximal edge 273, the outer edge 274, and the distal edge 275 may collectively define an outer spine of the stent engaging member 270. The outer spine may extend between the first surface 271 and the second surface 272 of the stent engaging member 270.

The proximal edge 273 may include an inner end positioned adjacent to the sleeve 262 and an outer end opposite the inner end. The proximal edge 273 may extend outward away from the sleeve 262. Additionally, or alternatively, the proximal edge 273 may extend longitudinally relative to the sleeve 262. For example, the proximal edge 273 may extend radially outward and longitudinally in a proximal direction from the sleeve 262 such that an acute angle θ is formed between the proximal edge and the sleeve as shown in FIG. 4. Alternatively, the proximal edge may extend radially outward and longitudinally in a distal direction from the sleeve 262 such that an obtuse angle is formed between the proximal edge and the sleeve. In another example, the proximal edge may extend outward in a direction that is substantially perpendicular to the sleeve 262 such that a right angle is formed between the proximal edge and the sleeve 262.

The stent engaging member 270 may include a projection 277 extending from the proximal edge 273. The projection 277 may extend longitudinally from the proximal edge 273 in a proximal direction as shown in FIG. 4. The projection 277 may extend from the outer end of the proximal edge 273. The projection 277 may be configured to be received within a portion of a prosthesis to retain the prosthesis in a partially expanded configuration as further described below. A notch 279 may be positioned between the projection 277 and the outer surface of the sleeve 262. The notch 279 may have three sides defined by the sleeve 262, the proximal edge 273 of the stent engaging member 270, and the projection 277 (e.g., the radially innermost edge of the projection), respectively. The notch 279 may include an opening positioned radially between the proximal tip of the projection 277 and the sleeve 262. A portion of the prosthesis may be received within the notch 279 to retain the prosthesis in the partially expanded configuration as further described below.

The outer edge 274 may extend longitudinally relative to the sleeve 262 between the proximal edge 273 and the distal edge 275. In one example, the outer edge 274 may be substantially parallel to the outer surface and/or the longitudinal axis of the sleeve 262 as shown in FIG. 4. In other examples, the outer edge may be positioned at any angle relative to the sleeve 262. The outer edge 274 may define the radially outermost portion of the stent engaging member 270. To that end, the outer edge 274 may be joined to the outer end of the proximal edge 273 and the outer end of the distal edge 275. The outer edge 274 may be coextensive with the outer portion of the projection 277. In other words, the outer edge 274 may abut or define the radially outermost edge of the projection 277.

The distal edge 275 may include an inner end positioned adjacent to the sleeve 262 and an outer end opposite the inner end. The distal edge 275 may extend outward away from the sleeve 262. Additionally, or alternatively, the distal edge 275 may extend longitudinally relative to the sleeve 262. For example, the distal edge 275 may extend radially outward and longitudinally in a proximal direction such that an obtuse angle φ is formed between the distal edge and the sleeve 262 as shown in FIG. 4. In this manner, the distal edge 275 may form a tapered distal surface of the stent engaging member 270. Such a tapered distal surface may reduce the tendency of the stent engaging member 270 to catch or snag on a portion of the prosthesis or the introducer during deployment of the prosthesis as further described below. The distal edge 275 may extend in a substantially straight line from the inner end to the outer end of the distal edge. Alternatively, the distal edge may be curved between the inner end and the outer end of the distal edge. Such a curve may be concave or convex. In another example, the distal edge may extend radially outward and longitudinally in a distal direction such that an acute angle is formed between the distal edge and the sleeve 262. In another example, the distal edge may extend outward in a direction that is substantially perpendicular to the sleeve 262 such that a right angle is formed between the distal edge and the sleeve 262.

The stent engaging member 270 may be dimensioned to engage the stent 105 of the stent graft 100 as further described below. To that end, the stent engaging member 270 may have a thickness (e.g., between the first surface 271 and the second surface 272) between about 0.178 mm (0.007 in) and about 0.762 mm (0.03 in), typically between about 0.356 mm (0.014 in) and about 0.508 mm (0.02 in). Additionally, or alternatively, the stent engaging member 270 may have a length (e.g., between the inner end of the distal edge 275 and the proximal end of the projection 279) between about 1.25 mm and about 5.25 mm, typically between about 2.5 mm and about 3.5 mm. Additionally, or alternatively, the stent engaging member 270 may have a height (e.g., between the outer surface of the sleeve 262 and the outer edge 274) between about 1 mm and about 2 mm, typically between about 1.25 mm and about 1.5 mm. In other examples, the stent engaging member may have any size or shape suitable for engaging a prosthesis to retain at least a portion of the prosthesis in a partially expanded configuration.

Figure 5:
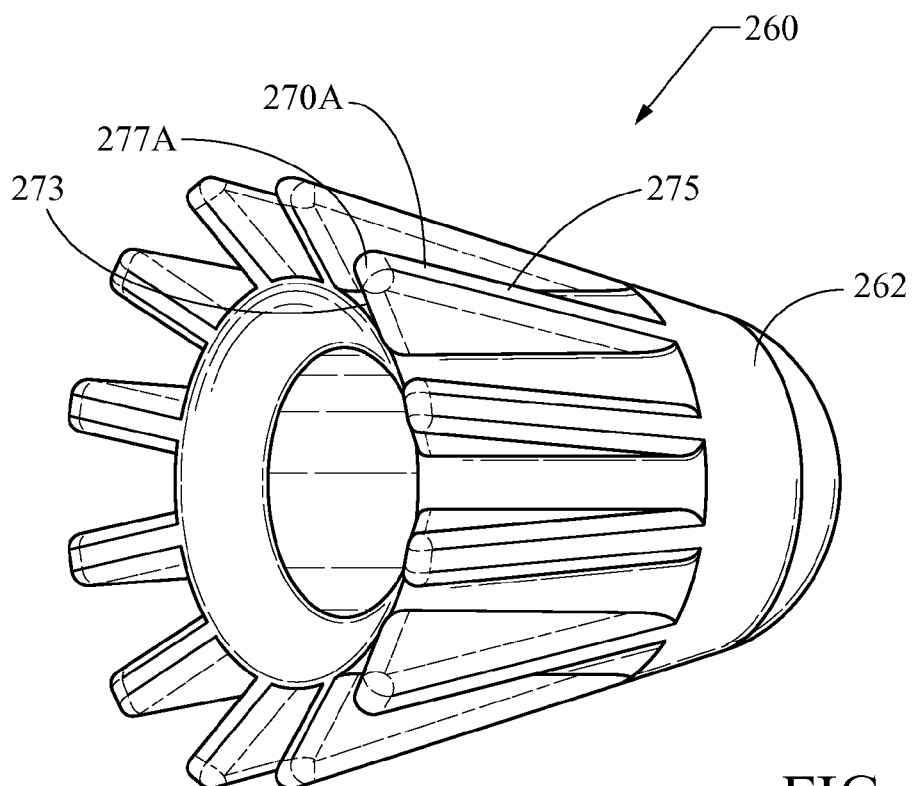
FIG. 5 illustrates another example of a stent retaining member.

FIG. 5 illustrates another example of the stent retaining member 260 including a stent engaging member 270A. The stent engaging member 270A may be similar to the stent engaging member 270 described above. For example, the stent engaging member 270A may include the proximal edge 273 and the distal edge 275. The outer edge 274 may be omitted such that the outer end of the proximal edge 273 and the outer end of the distal edge 275 meet one another to form a point 277A. The point 277A may be configured to engage a portion of a prosthesis as described herein with reference to the projection 277. The distal edge 275 may taper from the sleeve 260 to the point 277A. In one example, the distal edges 275 of a plurality of stent engaging members 270A may collectively form a frustoconical outer surface of the stent retaining member 260. Additionally, or alternatively, a distal portion of the sleeve 262 may be tapered as shown in FIG. 5. In one example, the taper of the proximal portion of the sleeve may be substantially the same as the taper of the distal edge 275. In this manner, a smooth taper may be formed from the distal end of the sleeve to the point 277A of the stent engaging member 270A. This may reduce the tendency of the stent retaining member 260 to snag on the deployed prosthesis during withdrawal as described herein. Additionally, or alternatively, the sleeve 262 of FIG. 5 may extend proximally beyond the point 277A to engage the proximal tip 240 and/or the inner cannula 250 as described above with reference to FIG. 4. Additionally, or alternatively, the sleeve 262 of FIG. 5 may include an attachment mechanism as described above with reference to FIG. 4.

The stent retaining member 260 shown in FIG. 5 may be made by forming a tubular member having a frustoconical shape. Such a tubular member may be formed, for example, by machining. The stent engaging members 270A may be formed by removing the portions of the frustoconical tubular member between adjacent stent engaging members. For example, portions of the tubular member may be removed by machining (e.g., electrical discharge machining (EDM) or wire EDM) to form the stent engaging members 270A. In this manner, the outer surfaces of the stent engaging members may have the frustoconical shape described above. Edges of the stent engaging members 270A may be machined to reduce the sharpness of the edges (e.g., to smooth the edges).

Figure 6:
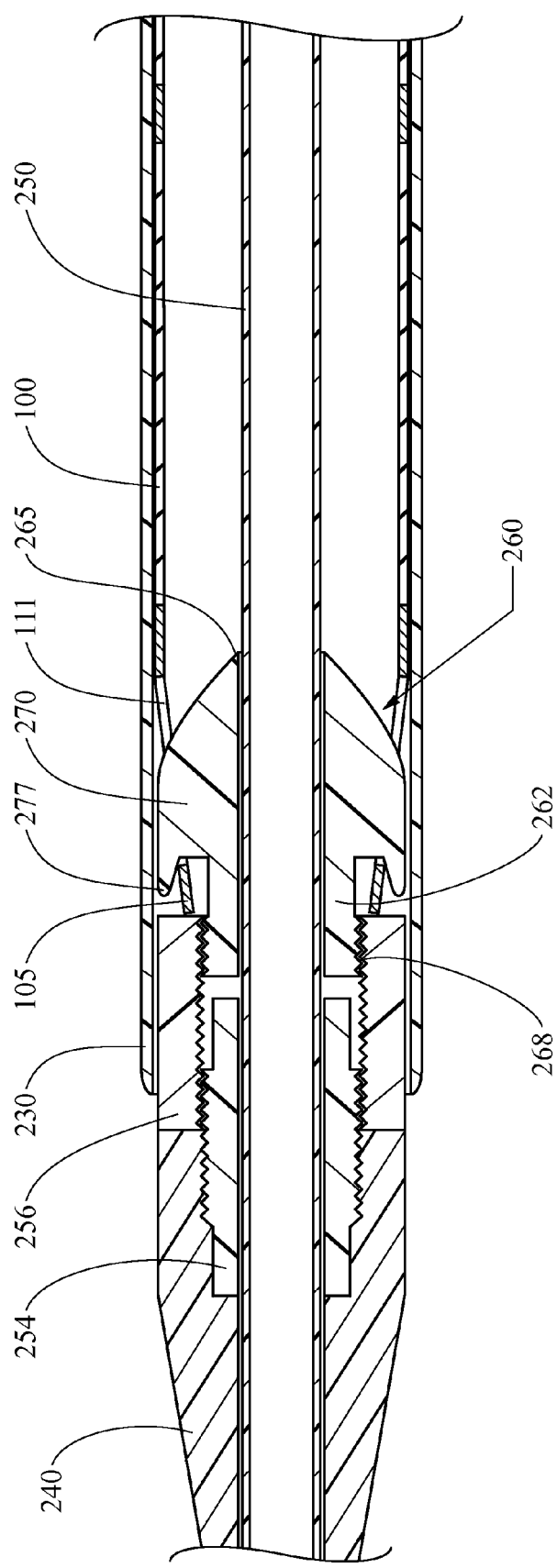
FIG. 6 is a longitudinal cross sectional view of a proximal portion of the introducer of FIG. 3 with the stent graft of FIG. 1 loaded on the introducer.

FIG. 6 is a partial longitudinal cross sectional view of a proximal portion of one embodiment of the introducer 200 with the stent graft 100 loaded on the introducer. The stent graft 100 may be positioned within the lumen of the sheath 230 in a conventional manner to retain the stent graft in a compressed, delivery configuration. The stent 105 of the stent graft 100 may be engaged by the stent retaining member 260 as further described below. The inner cannula 250 may include a threaded insert 254 attached to or integral with the proximal end of the inner cannula. The threaded insert 254 may include external threads configured to engage internal threads of the proximal tip 240 to couple the inner cannula 250 to the proximal tip. Additionally, or alternatively, the proximal tip 240 may be molded onto the inner cannula 250 and the threaded insert 254 to couple the inner cannula to the proximal tip. A coupling member 256 may be attached to the inner cannula 250 and/or the proximal tip 240 near the proximal end of the inner cannula. The coupling member 256 may be configured as a substantially cylindrical tubular member having internal threads. The coupling member 256 may be threadably engaged with the threaded insert 254 as shown in FIG. 6. The coupling member 256 and the proximal tip 240 may be joined to one another by the threaded insert 254 such that the coupling member forms a distal portion of the proximal tip to engage the stent 105 as further described below. Additionally, or alternatively, the distal end of the proximal tip 240 may include a threaded portion having external threads, and the internal threads of the coupling member 256 may be engaged with the external threads of the proximal tip. Additionally, or alternatively, the coupling member 356 may be integral with the proximal tip 240. In other words, the distal portion of the proximal tip 240 may include the coupling member 256.

The coupling member 256 may be fixedly attached (e.g., bonded or welded) to the threaded insert 254, the inner cannula 250, and/or the proximal tip 240. In this manner, rotation and/or translation of the inner cannula 250 and the proximal tip 240 relative to the stent retaining member 260 may cause a corresponding rotation and/or translation of the coupling member 256 relative to the stent retaining member. The coupling member 256 may extend distally to engage the stent retaining member 260. For example, the threaded segment 268 of the sleeve 262 of the stent retaining member 260 may be engaged with the internal threads of the coupling member 256 as shown in FIG. 6.

The stent retaining member 260 may engage the stent graft 100 to retain the stent graft in a partially expanded configuration after withdrawal of the sheath 230 as further described below. For example, the stent retaining member 260 may engage the stent 105 of the stent graft 100 as shown in FIG. 6. The stent engaging member 270 of the stent retaining member 260 may engage an apex of the stent 105. For example, the stent engaging member 270 may engage an opening or aperture of the apex, a bend of the apex positioned between two adjacent struts, or any other portion of the apex. The stent engaging member 270 of the stent retaining member 260 may extend through an opening in the stent 105. For example, the stent 105 may include one or more apertures 111 (e.g., eyelets) positioned near the proximal end of the stent as described above with reference to FIG. 2. The stent engaging member 270 may extend through the aperture 111 as shown in FIG. 6. The projection 277 of the stent engaging member 270 may be positioned radially outward of the stent 105. The proximal end 107 of the stent 105 may be positioned adjacent to or in abutting contact with the distal surface of the coupling member 256, which may form the distal surface of the proximal tip 240. In this manner, the engaged portion of the stent 105 may be prevented from moving proximally relative to the introducer 100 by the coupling member 256. The projection 277 of the stent engaging member 270 may be longitudinally aligned with at least a portion of the proximal portion of the stent 105. In other words, the projection 277 may hook the proximal end of the stent 105 as shown in FIG. 6. The proximal portion of the stent 105 (e.g., the portion of the stent positioned proximal of the aperture 111) may be at least partially positioned within the notch 279 of the stent engaging member 270. In this manner, the engaged portion of the stent 105 may be prevented from moving radially outward by the projection 277. The proximal portion of the stent 105 may be captured between the stent retaining member 260 and the coupling member 256. The other stent engaging members 270 of the stent retaining member 260 may engage other apices of the stent 105 in a similar manner. The stent engaging member 270 may push the slots and tips of the top stent (e.g., the stent 105) proximally and wedge them against the distal end of the coupling member 256 and/or the nose cone (e.g., the proximal tip 240). In one example, each apex of the stent 105 may be engaged by a corresponding stent engaging member 270. In other words, each apex of the stent 105 may be captured by the stent retaining member 260. In other examples, a portion of the apices (e.g., every other apex) of the stent may be engaged by a corresponding stent engaging member 270. The engaged apices may be prevented from moving radially outward relative to the stent retaining member 260 such that the stent 105 is prevented from expanding to a fully expanded configuration.

In other examples, the stent engaging member 170 may engage any other portion of the stent graft 100. For example, the stent engaging member 270 may extend through an opening between adjacent struts of the stent to engage the bend positioned between the struts. The stent retaining member 260 may be unattached to the handle 202 of the introducer 100. In one example, the distal end 265 of the sleeve 262 may be positioned within the lumen of the stent graft 100. In other words, the stent retaining member 260 may not extend distally beyond the distal end of the stent graft 100. In other examples, the sleeve may extend distally to the handle of the introducer as described below.

Figure 7:
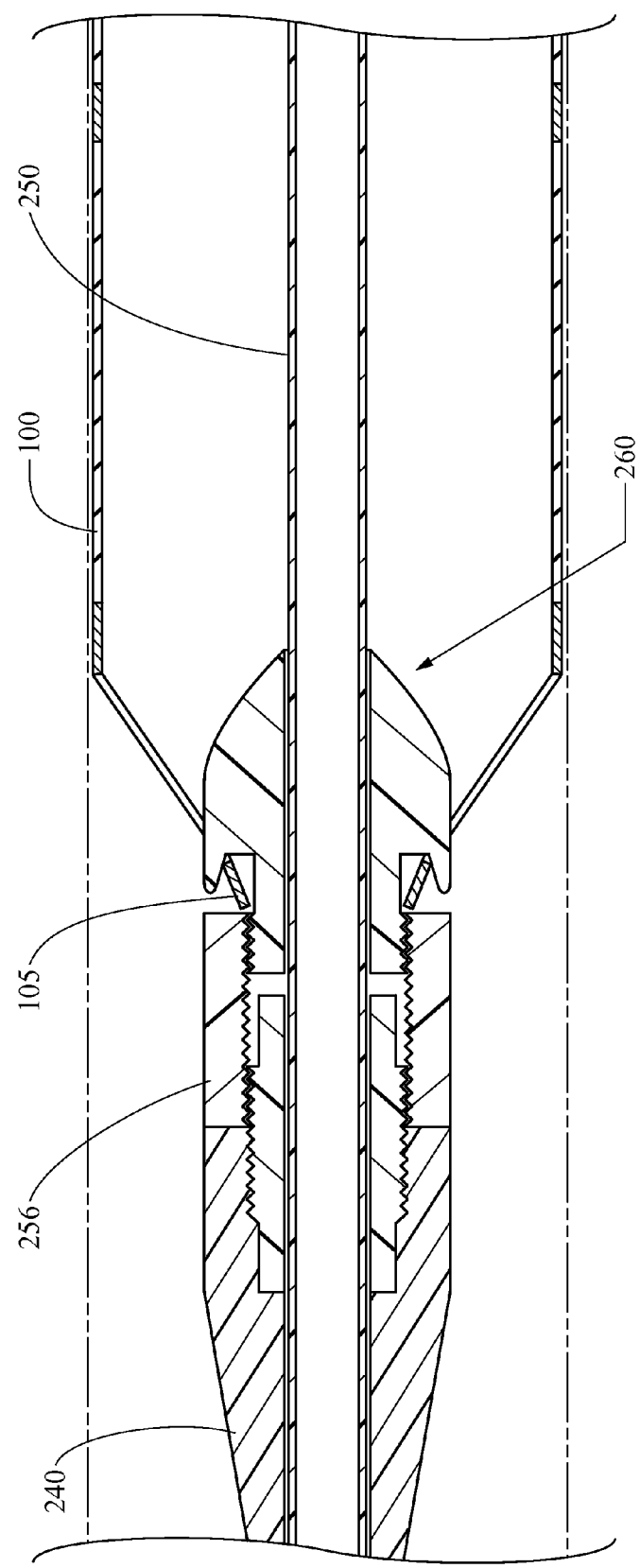
FIG. 7 is a longitudinal cross sectional view of the proximal portion of the introducer of FIG. 3 with a sheath retracted to partially deploy the stent graft.

The introducer 200 with the stent graft 100 loaded on the introducer may be advanced within a body vessel of a patient in a conventional manner to position the stent graft at a target location within the body vessel. The sheath 230 may be retracted distally relative to the inner cannula 250 to expose the stent graft 100 as shown in FIG. 7. Upon retraction of the sheath 230, the stent graft 100 may expand radially outward to a partially expanded configuration. For example, a distal portion of the stent graft 100 (e.g., the portion of the stent graft distal of the stent 105) may expand radially outward. The distal portion of the stent graft 100 may contact the wall of the body vessel as shown in FIG. 7. The stent 105 may remain engaged by the stent retaining member 260 as described above. In this manner, the stent 105 may be prevented from expanding to the fully expanded configuration. In other words, the stent 105 may not fully expand to engage the wall of the body vessel. This may enable repositioning of the stent graft 100 within the body vessel (e.g., by translating the introducer 100 proximally or distally relative to the body vessel) prior to complete deployment of the stent graft.

The stent 105 may be released from the stent retaining member 260 to fully deploy the stent graft 100. In one example, the inner cannula 250 may be rotated relative to the stent graft 100. The inner cannula 250 may be rotated by rotating the handle 202 of the introducer 200. Such rotation of the inner cannula 250 may cause a corresponding rotation of the coupling member 256. The inner cannula 250 may be rotatably and slidably received within the lumen 266 of the sleeve 262 of the stent retaining member 260 as described above. Upon rotation of the inner cannula 250 and the coupling member 256, the stent retaining member 260 may be substantially prevented from rotating by the engagement between the stent retaining member and the stent 105. In other words, the engagement (e.g., the frictional force) between the distal portion of the stent graft 100 and the wall of the body vessel may substantially prevent the stent graft 100 from rotating within the body vessel, and the engagement between the stent 105 and the stent retaining member 260 may substantially prevent the stent retaining member 260 from rotating relative to the stent graft. The position of the stent retaining member 260 may be substantially fixed relative to the engaged stent graft 100. Rotation of the inner cannula 250 and the coupling member 256 relative to the stent graft 100 may cause a corresponding rotation of the inner cannula and the coupling member relative to the stent retaining member 260.

Figure 8:
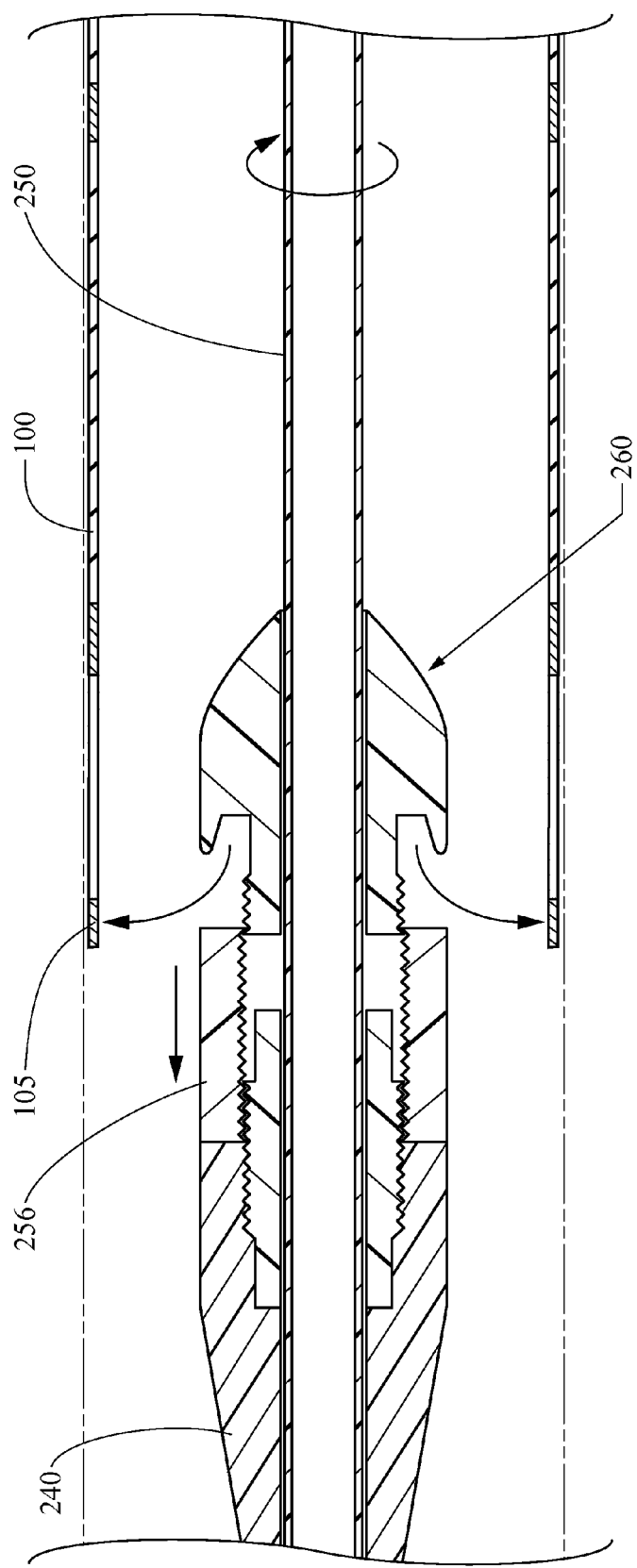
FIG. 8 is a longitudinal cross sectional view of the proximal portion of the introducer of FIG. 3 with the stent graft fully deployed.

Upon rotation of the coupling member 256 relative to the stent retaining member 260, the coupling member and the sleeve 262 of the stent retaining member may unthread from one another. Such unthreading may cause the coupling member 256 to move proximally relative to the stent retaining member 260 as shown in FIG. 8. The inner cannula 250, the coupling member 256, and the proximal tip 240 may move proximally as a unit relative to the stent retaining member 260. Upon proximal movement of the coupling member 256 relative to the stent retaining member 260, the distance between the distal face of the coupling member and the stent engaging member 270 may increase. The coupling member 256 may be rotated relative to the stent retaining member 260 until the engaged proximal portion of the stent 105 is capable of passing through the space between the projection 277 of the stent engaging member 270 and the distal face of the coupling member 256. In other words, the coupling member 256 may be rotated relative to the stent retaining member 260 until the distance between the distal face of the coupling member and the stent engaging member 270 is sufficient to release the stent 105 of the stent graft 100.

In one example, in response to rotation of the inner cannula 250 with respect to the stent retaining member 260, the proximal tip 240 (e.g., the coupling member 256 of the proximal tip) may be longitudinally movable relative to the stent engaging member 270 between a retaining configuration as shown in FIGS. 6-7 and a releasing configuration as shown in FIG. 8. The longitudinal distance between the stent engaging member 270 and the proximal tip 240 in the retaining configuration may be less than the longitudinal distance between the stent engaging member and the proximal tip in the releasing configuration. In other words, the proximal tip 240 and the stent engaging member 270 may be spaced from one another by a greater longitudinal distance in the releasing configuration than in the retaining configuration. In this manner, the stent engaging member 270 and the proximal tip 240 in the retaining configuration may be configured to capture and/or retain the stent 105. Additionally, or alternatively, the stent engaging member 270 and the proximal tip 240 in the releasing configuration may be configured to release the stent 105.

Upon release from the stent retaining member 260, the stent 105 may expand to the expanded configuration to engage the wall of the body vessel. The threaded segment 268 of the sleeve 262 of the stent retaining member 260 may have a sufficient length that the stent retaining member and the coupling member 256 may remain engaged with one another after release of the stent 105 as shown in FIG. 8. This may prevent the stent retaining member 260 from translating freely (e.g., sliding proximally and/or distally) along the inner cannula 250 after release of the stent 105. Alternatively, the stent retaining member 260 and the coupling member may be disengaged from one another following release of the stent 105. Additionally, or alternatively, the threaded segment 268 may have a sufficient length that the engagement (e.g., the threaded engagement) between the retaining member 260 and the coupling member 256 is sufficiently strong to withstand longitudinal pulling forces which may be experienced during loading and/or deployment of the stent graft 100.

While FIGS. 6-8 show a stent retaining member configured generally as described in FIG. 4, the principles described in connection with FIGS. 6-8 are equally applicable to introducer embodiments with stent retaining members and/or coupling members having different configurations such as, for example, those shown in FIGS. 5 and 9-12.

In any of the embodiments described herein, the retaining member and the coupling member may be formed from any suitable material. The retaining member and the coupling member may be formed from the same or different materials. In one example, the retaining member and/or the coupling member may be formed from stainless steel. The retaining member and/or the coupling member may be formed using any suitable process such as, for example, machining or stamping. Using a stamping process may reduce the cost of producing and/or assembling the introducer. The retaining member or a portion thereof (e.g., the engaging members) may be heat treated to increase the strength of the retaining member. In other examples, the retaining member and the coupling member may be formed from any other suitable materials such as, for example, metallic materials or polymeric materials.

FIGS. 9-10 illustrate another embodiment of the coupling member 256 and the stent retaining member 260. The coupling member 256 may include a proximal portion 257 and a distal portion 258. The proximal portion 257 may be configured as a chamber to receive a portion of the stent retaining member 260 as further described below. To that end, the proximal portion 257 may include a lumen 257A extending longitudinally within the coupling member 256. Additionally, or alternatively, the distal portion may be configured as a tubular segment extending distally from the chamber. To that end, the distal portion 258 may include a lumen 258A extending longitudinally within the coupling member 256. The lumen 257A of the proximal portion 257 and the lumen 258A of the distal portion 258 may be in fluid communication with one another. The lumen 257A of the proximal portion 257 may have a larger diameter than the lumen 258A of the distal portion 258. The inner wall of the distal portion 258 may include threads to engage the stent retaining member 260 as described above. The inner wall of the proximal portion 257 may be substantially smooth. A resilient member, such as a spring 259, may be positioned within the lumen 257A of the proximal portion 257 of the coupling member 256. The spring 259 may surround the inner cannula 250 as shown in FIG. 9. The spring 259 may engage the stent retaining member 260 to push the stent retaining member distally relative to the coupling member 256 as further described below.

The sleeve 262 of the stent retaining member 260 may include a proximal sleeve portion 269 extending proximally beyond the threaded segment 268. The proximal sleeve portion 269 may have a substantially smooth outer surface. Additionally, or alternatively, the proximal sleeve portion 269 may have a smaller diameter than the threaded segment 268. This may enable the proximal sleeve portion 269 to slide proximally and/or distally within the threaded distal portion 258 of the coupling member 256. In one example, the sleeve 262 of the stent retaining member 260 may be configured as a piston member. To that end, the sleeve 262 may include a crown member 269A positioned at the proximal end of the proximal sleeve portion 269. The crown member 269A may have a larger diameter than the proximal sleeve portion 269. In one example, the diameter of the crown member 269A may correspond to (e.g., may be substantially the same as or slightly smaller than) the diameter of the lumen 257A of the proximal portion 257 of the coupling member 256.

The spring 259 may be positioned longitudinally between the crown member 269A and the proximal wall of the coupling member 256. The spring 259 may engage the crown member 269A of the stent retaining member 260 to push the stent retaining member distally relative to the coupling member 256. In other words, the spring 259 may bias the crown member 269A of the stent retaining member toward the distal end of the lumen 257A of the proximal portion 257 of the coupling member 256. The crown member 269A may have a larger diameter than the lumen 258A of the distal portion 258 of the coupling member 256. In this manner, the crown member 269A of the stent retaining member 260 may be captured within the lumen 257A of the proximal portion 257 of the coupling member 256. The stent retaining member 260 may be threadably engaged with the coupling member 256 such that the spring 259 is compressed as shown in FIG. 9. The stent retaining member 260 and the coupling member 256 may be unthreaded from one another by rotating the inner cannula 250 as described above. The threaded segment 268 of the stent retaining member 260 may be disengaged from the coupling member 256. The coupling member 256 may move proximally relative to the stent retaining member 260, and the proximal sleeve portion 269 of the stent retaining member may slide within the lumen 258A of the distal portion 258 of the coupling member until the crown member 269A contacts the distal end of the proximal portion 257 of the coupling member as shown in FIG. 10. In this manner, the stent retaining member 260 may be maintained within the prosthesis retention section of the introducer 200 after disengagement from the coupling member 256. In other words, proximal translation of the stent retaining member 260 relative to the inner cannula 250 may be substantially prevented by the spring 259. Additionally, or alternatively, distal translation of the stent retaining member 260 relative to the inner cannula 250 may be substantially prevented by the engagement between the coupling member 256 and the crown member 269A of the stent retaining member. The biasing force of the spring 259 against the stent retaining member 260 may aid in moving the coupling member 256 proximally relative to the stent retaining member during release of the engaged stent 105 as described above.

Figure 11:
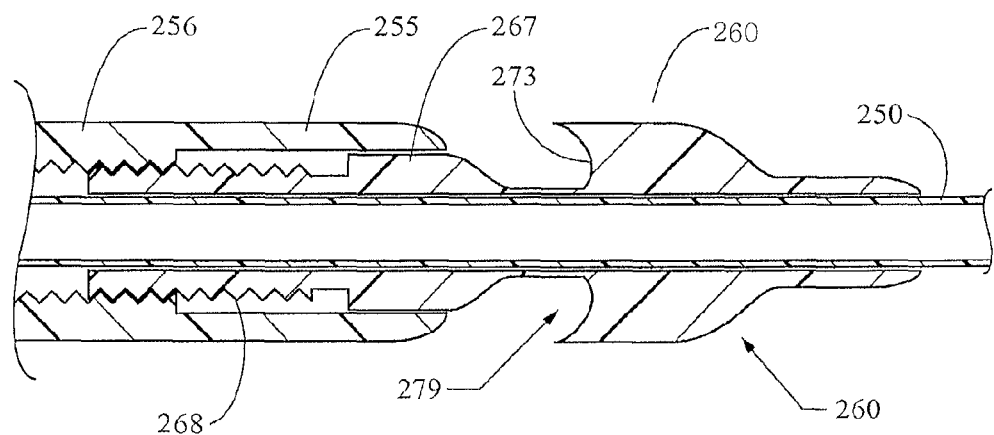
FIG. 11 is a longitudinal cross sectional view of a proximal portion of another example of an introducer having a stent retaining member.

FIG. 11 illustrates another embodiment of the coupling member 256 and the stent retaining member 260. The coupling member 256 may include a distal extension portion 255. The distal extension portion 255 may be positioned distal of the threaded portion of the coupling member 256. The distal extension portion 255 may be unthreaded as shown in FIG. 11. In other words, the inner wall of the distal extension portion 255 may be substantially smooth. The sleeve 262 of the stent retaining member 260 may include an insert segment 267 positioned longitudinally between the proximal end of the stent engaging member 270 and the distal end of the threaded segment 268. The insert segment may include a proximal portion and a distal face. The proximal portion of the insert segment 267 may be configured as a substantially cylindrical tubular member having an outer diameter corresponding to (e.g., substantially the same as or slightly smaller than) the inner diameter of the distal extension portion 255 of the coupling member 256. The diameter of the proximal portion of the insert segment 267 may be larger than the diameter of the threaded segment 268 and/or the portion of the sleeve 262 positioned distal of the insert segment. The distal face of the insert segment 267 may be configured as a tapered distal surface having a first diameter that is substantially the same as the diameter of the proximal portion of the insert segment and a second diameter that is substantially the same as the portion of the sleeve 262 positioned distal of the insert segment. In other words, the distal face of the insert segment 267 may taper from the diameter of the proximal portion of the insert segment to the diameter of the portion of the sleeve positioned distal of the insert segment.

With the stent retaining member 260 threaded into the coupling member 256 as described above, the insert segment 267 may be positioned within the distal extension portion 255 of the coupling member. In one example, substantially the entire insert segment 267 may be positioned within the coupling member such that no portion of the insert segment extends distally beyond the distal end of the coupling member. The stent engaging members 270 may engage the distal facing surface of the coupling member 256. In one example, the proximal edge 273 of the stent engaging members 270 may be curved as shown in FIG. 11. Additionally, or alternatively, the distal facing surface of the coupling member 256 may be curved. The radius of curvature of the proximal edge 273 may be substantially the same as the radius of curvature of the distal facing surface of the coupling member 256 such that the proximal edge of the stent engaging member 270 and the distal facing surface of the coupling member 256 may engage one another along the curved surfaces to capture the stent 105 within the notch 279 as described above. In other examples, the distal facing surface of the coupling member 256 may be configured as a substantially flat or blunt surface as described above.

Upon moving the coupling member 256 proximally relative to the stent retaining member 260 (e.g., by rotation of the coupling member as described above), the distal face of the insert segment 267 may exit the coupling member as shown in FIG. 11. In other words, the distal face of the insert segment 267 may extend distally beyond the distal facing surface of the coupling member 256. The tapered distal face of the insert segment 267 may provide a relatively smooth, tapered surface to guide the engaged portion of the stent 105 out of engagement with the stent retaining member 260 to deploy the stent. In other words, the tapered distal face of the insert segment may form a smooth transition against which the apices of the stent 105 may slide during deployment of the stent. This may help to prevent catching or snagging the stent 105 on the coupling member 256 and/or the stent retaining member 260 during deployment of the stent.

Additionally, or alternatively, the introducer 200 may include a retaining member and/or a coupling member having any other suitable configuration. For example, the introducer 200 may include a retaining member having any suitable configuration such as, for example, any of those described below with reference to FIGS. 13-14. Additionally, or alternatively, the retaining member may engage one or more projections of the prosthesis, for example, as described below with reference to FIGS. 14 and 21-22. Additionally, or alternatively, the introducer 200 may include a coupling member having any suitable configuration such as, for example, any of those described below with reference to FIGS. 16-17 and 19.

The stent retaining member 260 has been described above with reference to an embodiment including 4 stent engaging members 270. However, this disclosure is not so limited. In other examples, the stent retaining member may include any number of stent engaging members.

Figure 12:
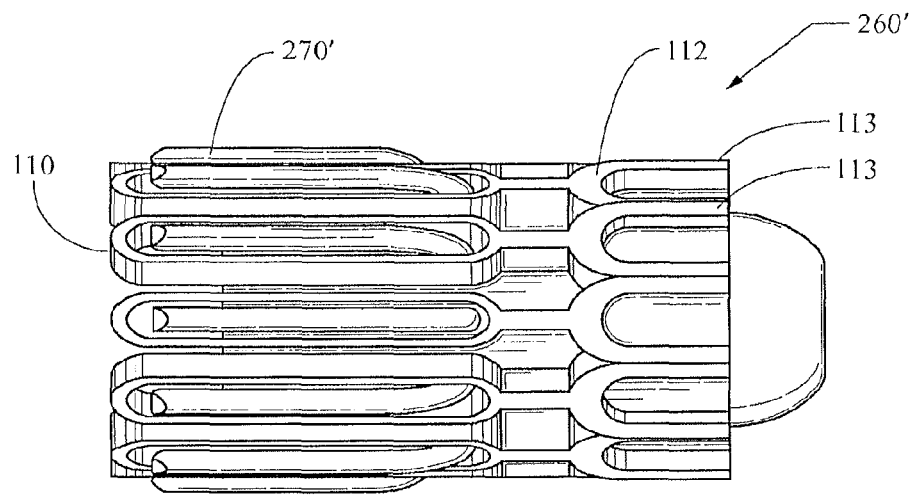
FIG. 12 illustrates another example of a stent retaining member engaging each of the apices of a stent.

FIG. 12 illustrates one embodiment of a stent retaining member 260' including 12 stent engaging members 270'. The stent engaging members 270' may be spaced from one another about the circumference of the sleeve of the stent retaining member 260'. For example, each stent engaging member 270' may be spaced from the adjacent stent engaging members by about 30 degrees with respect to the circumference of the sleeve. Each stent engaging member 270' may be engaged with an eyelet positioned at the proximal end of the stent 105. In one example, the stent 105 may include 12 eyelets, and each eyelet may be engaged by a stent engaging member 270' as shown in FIG. 12. In this manner, all 12 points of the stent 105 may be captured by the stent retaining member 260'. In one example, each end region 110 of the stent 105 may be configured as an extended stent eyelet extending proximally from the bend 112 between two adjacent struts 113 as described above. In one example, the extended stent eyelet may have a length of between about 1.8 mm and about 5.4 mm. The extended stent eyelet may fit snugly between the stent engaging members 270' and leave enough clearance so that, as the stent engaging member moves away from the coupling member 256, the extended eyelets become free.

Capturing each stent eyelet with the stent engaging member may prevent damaging the stent 105 during retraction of the sheath. For example, uncaptured apices may catch or snag on the sheath and be bent backward during retraction of the sheath. Capturing each stent eyelet may avoid such catching or snagging. Additionally, or alternatively, capturing each stent eyelet with the stent engaging member may prevent uncaptured stent points from standing out (e.g., extending radially outward away from the sleeve) following retraction of the sheath. This may prevent uncaptured apices and/or projections (e.g., barbs or tabs) positioned on uncaptured apices from engaging the vessel wall prior to full deployment of the stent. This may enable the physician to reposition the stent graft (e.g., by pushing or pulling the stent graft) without bending the uncaptured apices and/or damaging the vessel wall after retracting the sheath and before fully deploying the stent.

In other examples, the stent retaining member may include any number of stent engaging members, and the stent may include any number of eyelets. The number of stent engaging members and/or the number of eyelets may depend on the size of the stent graft. For example, a 12 point fin (e.g., a stent retaining member including 12 stent engaging members) may be configured to capture all stent points on a 36 mm or larger prosthesis (e.g., a stent graft having a diameter of greater than or equal to about 36 mm). Additionally, or alternatively, such a 12 point fin may be configured for a 13 Fr delivery system. In another example, a stent retaining member including 10 stent engaging members may be configured to capture all stent points on a 32 mm prosthesis. In another example, a stent retaining member including 8 stent engaging members may be configured to capture all stent points on a 26 mm prosthesis. In other examples, a prosthesis having any diameter may include any number of stent points and/or eyelets.

Additionally, or alternatively, the dimensions (e.g., thickness, length, and/or height) of the stent engaging member may depend on the number of stent engaging members included on the stent retaining member. For example, each stent engaging member of a stent retaining member including 6 stent engaging members may have a thickness of about 0.02 in. Additionally, or alternatively, each stent engaging member of a stent retaining member including 12 stent engaging members may have a thickness of about 0.014 in. Reducing the thickness of each stent engaging member as the number of stent engaging members increases may enable tighter packing of the stent eyelets to aid in retaining the stent in the compressed configuration.

Figure 13:
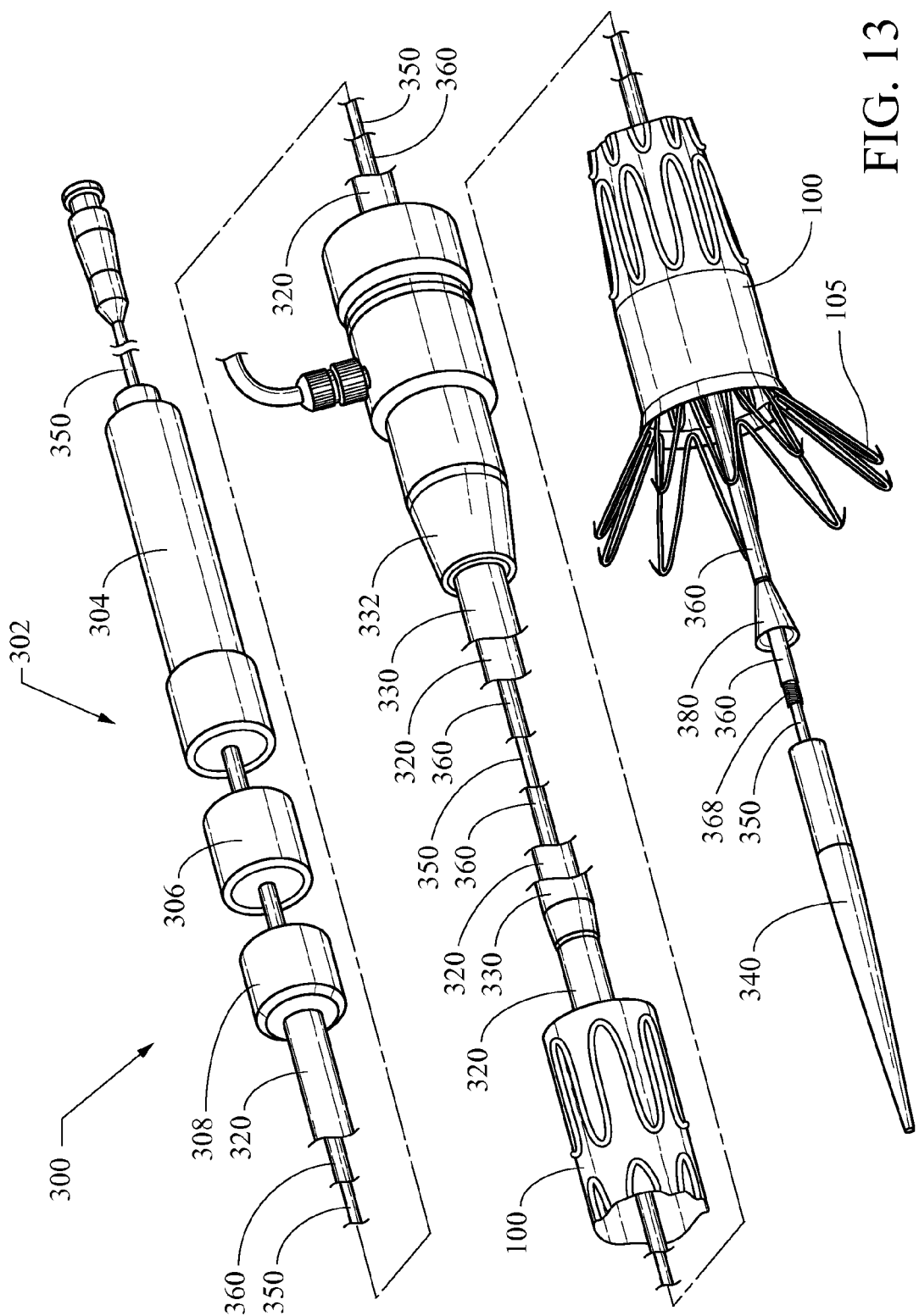
FIG. 13 illustrates another example of an introducer.

FIG. 13 illustrates another embodiment of an introducer 300. The introducer 300 may be substantially similar to the introducer 200 in many respects. For example, the introducer 300 may include an inner cannula 350 extending generally longitudinally along at least a portion of the length of the introducer. A cannula handle 304 may be attached to the inner cannula 350 near the distal end of the inner cannula, and a proximal tip 340 may be attached to the inner cannula near a proximal end of the inner cannula.

The introducer may include a retaining member such as a stent retaining member including a sleeve and an engaging member such as a stent engaging member. The sleeve may be configured as a torque shaft 360 surrounding at least a portion of the inner cannula 350. The torque shaft 360 may extend generally longitudinally along at least a portion of the length of the introducer 300. A torque handle 306 may be attached to the torque shaft 360 near a distal end of the torque shaft. In some examples (e.g., where a sleeve or torque shaft segment is substituted for the torque shaft 360 as further described below), the torque shaft handle 306 may be omitted. The stent engaging member may be configured as a deployment member 380 attached to the torque shaft 360 near the proximal end of the torque shaft. The deployment member 380 may be configured to engage a prosthesis (e.g., the stent graft 100) as further described below. To that end, the torque shaft 360 and the deployment member 380 may be configured to move relative to the inner cannula 350 as further described below.

A catheter, such as a pusher catheter 320, may surround at least a portion of the torque shaft 360 and the inner cannula 350. The pusher catheter 320 may extend generally longitudinally along at least a portion of the length of the introducer 300. A pusher handle 308 may be attached to the pusher catheter 320 near a distal end of the pusher catheter. In some examples (e.g., where the distal end 104 of the stent graft 100 may be unattached to the introducer 300 as further described below), the pusher catheter 320 and the pusher handle 308 may be omitted.

A sheath 330 may surround at least a portion of the torque shaft 360, the pusher catheter 320, and the inner cannula 350. The sheath 330 may extend generally longitudinally along at least a portion of the length of the introducer 300 to retain the prosthesis in a delivery configuration as further described below. A distal end of the sheath 335 may be attached to a sheath handle 332 which may aid in retracting the sheath to deploy the prosthesis as further described below.

Figure 14:
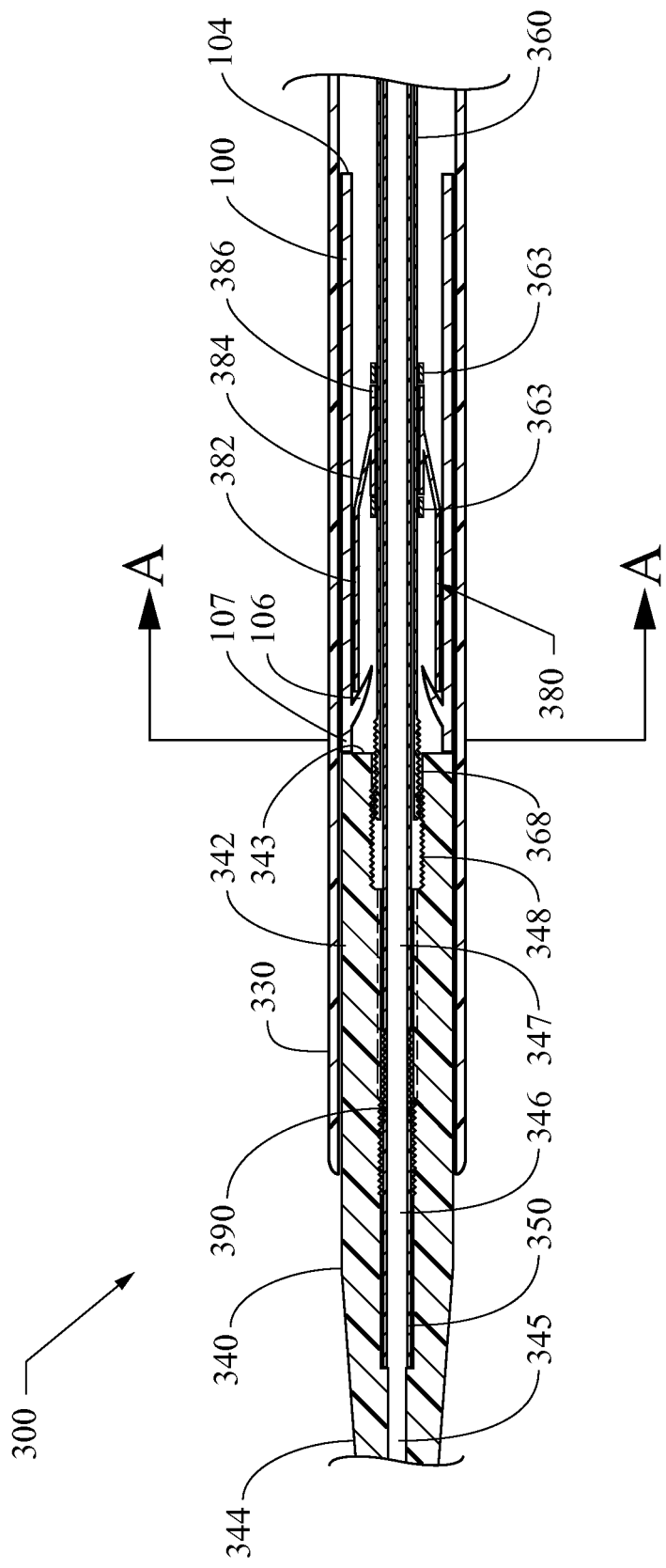
FIG. 14 is a longitudinal cross sectional view of a proximal portion of the introducer of FIG. 13 with the stent graft of FIG. 1 loaded on the introducer.

FIG. 14 is a partial longitudinal cross sectional view of a proximal portion of the introducer 300 with the stent graft 100 loaded in the introducer. The inner cannula 350 and the proximal tip 340 of the introducer 300 may be similar to those described in U.S. Pat. No. 7,435,253 to Hartley et al. and U.S. Patent Application Pub. No. 2011/0144735 by Hartley et al. which are incorporated by reference herein in their entirety. For example, the inner cannula 350 may be configured as an elongate tubular member having a generally cylindrical shape. A lumen may extend generally longitudinally within the inner cannula 350 between a proximal end and a distal end of the inner cannula. The lumen of the inner cannula 350 may be configured to receive a guide wire (not shown) to aid in navigating the introducer 300 to a desired location within the vasculature of a patient. The inner cannula 350 may be sufficiently flexible to enable the introducer 300 to be advanced within a relatively tortuous vessel such as the femoral artery.

The proximal tip 340 may be configured as a nose cone dilator. To that end, the proximal tip 340 may include a base portion 342 and an extension portion 344. The base portion 342 may be configured as a tubular member having a generally cylindrical shape. The extension portion 344 may extend proximally from the base portion 342. The extension portion 344 may be configured as a long, tapered, flexible extension having a generally conical shape. The tapered shape and flexibility of the extension portion 344 may aid in advancing the introducer 300 within a body vessel of the patient. A lumen may extend generally longitudinally within the proximal tip 340 between a proximal end and a distal end of the proximal tip. The diameter of the lumen may vary along the length of the proximal tip as further described below.

The proximal end of the proximal tip 340 may have a rounded, chamfered, or otherwise atraumatic shape to minimize trauma to a body vessel during introduction and navigation of the introducer 300 within the patient's body. Such an atraumatic tip also may minimize pain and/or discomfort to the patient during introduction and navigation of the introducer 300 within the patient's body. The outside diameter of the extension portion 344 of the proximal tip 340 may taper from a relatively small diameter at the proximal end of the proximal tip to a larger diameter at the base portion 342 of the proximal tip. The diameter of the base portion 342 of the proximal tip 340 may correspond to the inside diameter of the sheath 330 as further described below. A distal end of the base portion 342 of the proximal tip 340 may terminate in a blunt, distal facing surface 343. The surface 343 may be configured as a substantially planar surface positioned generally perpendicular to the longitudinal axis of the inner cannula 350. The surface 343 may be configured to engage a stent graft that may be loaded into the introducer 300 as further described below.

The inner cannula 350 may be removably attached to the proximal tip 340. Preferably, the inner cannula 350 may be fixedly attached to the proximal tip 340. The lumen of the inner cannula 350 may be in fluid communication with the lumen of the proximal tip 340 to form a continuous pathway extending between the proximal and distal ends of the introducer 300. In one example, the proximal end of the inner cannula 350 may be received within the lumen of the proximal tip 340 as shown in FIG. 14. The inner cannula 350 may be attached to the proximal tip 340 at a joint 390. The inner cannula 350 and the proximal tip 340 may be attached by any means. For example, the joint 390 may be configured as a threaded, friction, snap-fit, or any other type of connection. Additionally, or alternatively, the joint 390 may be formed by an adhesive that may be disposed between the inner cannula 350 and the proximal tip 340. In one example, the inner cannula 350 may include external threads configured to engage internal threads formed in the lumen of the proximal tip 340 at the joint 390. A portion of the proximal tip 340 may overlap a portion of the inner cannula 350 when the inner cannula is received within the proximal tip. Accordingly, the lumen of the proximal tip 340 may be sized and shaped to receive a portion of the inner cannula 350 as further described below. The inner cannula 350 may be received within the lumen of the proximal tip 340 to form a generally smooth and continuous lumen extending between the distal end of the inner cannula and the proximal end of the proximal tip.

As shown in FIGS. 13-14, the torque shaft 360 may be configured as an elongate tubular member having a generally cylindrical shape. A lumen may extend generally longitudinally within the torque shaft 360 between a proximal end and a distal end of the torque shaft. The torque shaft 360 may be sufficiently flexible to enable the introducer 300 to be advanced within a relatively tortuous vessel such as the femoral artery. The lumen of the torque shaft may be configured to receive the inner cannula 350. The distal end of the torque shaft 360 may be attached to the handle of the introducer 300 such that manipulation of the handle may cause the torque shaft to translate longitudinally with respect to the inner cannula 350. Additionally, or alternatively, manipulation of the handle may cause the torque shaft 360 to rotate about the longitudinal axis thereof. A low friction lining may be provided between the torque shaft 360 and the inner cannula 350 to enable the torque shaft to slide easily over the inner cannula. The low friction lining may be formed from any suitable material such as, for example, polytetrafluoroethylene (PTFE), sodium bicarbonate, a silicone lubricant, or any other biocompatible lubricant. Such a lining may be applied as a coating on the interior surface of the torque shaft 360, the exterior surface of the inner cannula 350, or both. Additionally, or alternatively, the torque shaft 360 and/or the inner cannula 350 may be formed from a low friction material to enable the torque shaft and the inner cannula to slide easily relative to one another.

The proximal end of the torque shaft 360 may be rotatably, slidably and/or releasably attached to the proximal tip 340. The torque shaft 360 may be configured to translate longitudinally relative to the proximal tip 340 as further described below. In one example, a portion of the torque shaft 360 may be received within the lumen of the proximal tip 340. The portion of the torque shaft 360 received with the lumen of the proximal tip 340 may be disposed radially between the inner cannula 350 and the proximal tip 340. In other words, a portion of the torque shaft 360 may be sandwiched between the inner cannula 350 and the proximal tip 340 when the torque shaft is attached to the proximal tip. To that end, a portion of the lumen of the proximal tip 340 extending from the distal end thereof may be sized and shaped to receive both the inner cannula 350 and the torque shaft 360 as further described below.

In one example, the proximal tip 340 may be molded onto the inner cannula 350. An annular space may be formed between the proximal tip 340 and the inner cannula 350 to receive the proximal end of the torque shaft 360 as described above. To that end, the proximal tip 340 may include a flared cannula (not shown). The flared cannula may be placed within the lumen of the proximal tip 340. The flared cannula may flare away from the inner cannula 350 to define the annular space between the inner cannula and the proximal tip 340. The flared cannula may include internal threads to engage the proximal end of the torque shaft 360 as described below.

The lumen of the proximal tip 340 may be sized and shaped to receive the inner cannula 350 and/or the torque shaft 360. For example, the lumen of the proximal tip 340 may include a first portion 345, a second portion 346 positioned distal of the first portion, and a third portion 347 positioned distal of the second portion. The first portion 345 may extend between the proximal end of the proximal tip 340 and the proximal end of the inner cannula 350. The diameter of the first portion 345 of the lumen of the proximal tip 340 may be substantially equal to the diameter of the lumen of the inner cannula 350 to provide a smooth transition from the lumen of the inner cannula to the lumen of the proximal tip. The second portion 346 of the lumen of the proximal tip 340 may extend between the proximal end of the inner cannula 350 and an intermediate point between the proximal end of the inner cannula and the distal end of the proximal tip. The intermediate point may be positioned at approximately the proximal end of the joint 390 between the inner cannula 350 and the proximal tip 340. The diameter of the second portion 346 may be greater than the diameter of the first portion 345. The increased diameter of the second portion 346 relative to the first portion 345 may correspond to a wall thickness of the inner cannula 350. In other words, the diameter of the second portion 346 of the lumen of the proximal tip 340 may be substantially equal to the outside diameter of the inner cannula 350. Additionally, or alternatively, the diameter of the second portion 346 may correspond to the outside diameter of the inner cannula 350 plus the thickness of any connecting means (e.g., threads or adhesive) between the inner cannula and the proximal tip 340 at the joint 390 as described above. The third portion 347 of the lumen of the proximal tip 340 may extend between the second portion 346 and the distal end of the proximal tip. The diameter of the third portion 347 may be greater than the diameter of the first portion 345 and the diameter of the second portion 346. The diameter of the third portion 347 may be sized to receive the inner cannula 350, the torque shaft 360, and any attachment means between the torque shaft and the proximal tip 340 as further described below.

The proximal end of the torque shaft 360 may be attached to the proximal tip 340 by any means. For example, the proximal end of the torque shaft 360 may include external threads 368 as shown in FIGS. 13-14. The external threads 368 may be configured to engage internal threads 348 formed within the lumen of the proximal tip 340. The internal threads 348 may extend along substantially the entire length of the third portion 347 of the lumen of the proximal tip 340 to enable longitudinal adjustment of the torque shaft 360 and the deployment member 380 relative to the proximal tip as further described below. The handle of the introducer 300 may be manipulated to rotate the torque shaft 360 about its longitudinal axis relative to the inner cannula 350, whereby the torque shaft may be threaded into and/or unthreaded from the proximal tip 340.

Figure 15:
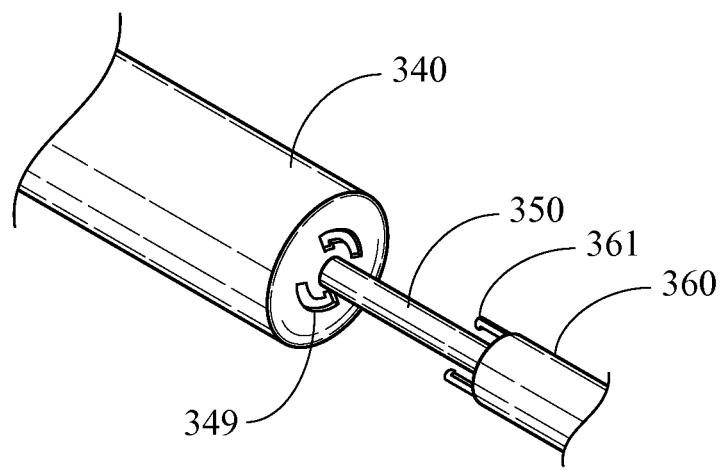
FIG. 15 illustrates one example of a system for coupling a torque shaft to a proximal tip.

In another example, the proximal end of the torque shaft 360 may be attached to the proximal tip 340 using a tab and slot arrangement as shown in FIG. 15. To that end, the torque shaft 360 may include one or more tabs 361 configured to engage corresponding slots 349 formed in the proximal tip 340. The tabs 361 may include enlarged tips configured to engage enlarged portions of the slots 349. The torque shaft 360 may be rotated relative to the proximal tip 340 to lock the tabs 361 into the slots 349. Additionally, or alternatively, the proximal end of the torque shaft 360 may be attached to the proximal tip 340 by any other attachment mechanism. For example, the attachment mechanism may include mechanical means such as, for example, threads, friction fit, snap fastener, ball and socket, spring or other resilient member, or the like. Additionally, or alternatively, the attachment mechanism may include any other attachment means (e.g., non-mechanical means) such as, for example, magnetic coupling, releasable adhesive, or the like. In other examples, the proximal end of the torque shaft 360 may be attached to the proximal tip 340 by a latch mechanism. Such a latch mechanism may be released by actuating a trigger wire attached to the latch mechanism. These and other known attachment means are contemplated by and within the scope of this disclosure.

Figure 16:
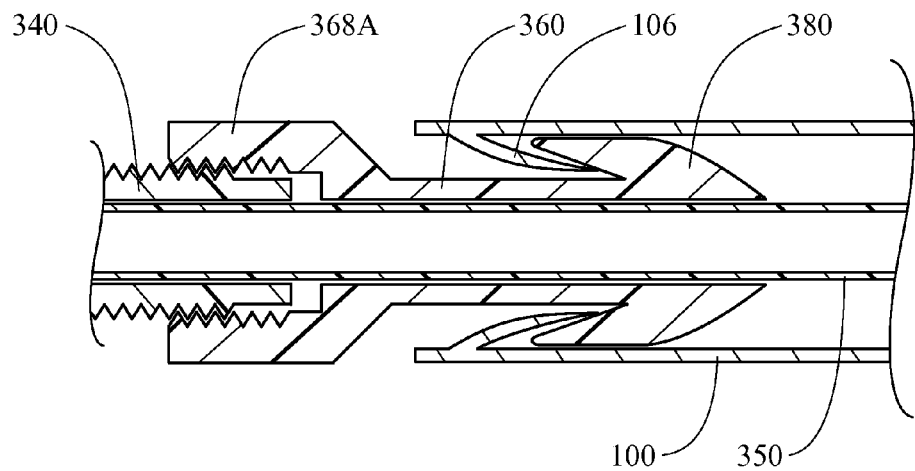
FIG. 16 is a longitudinal cross sectional view of a proximal portion of another example of an introducer.

FIG. 16 shows another example of the attachment of the torque shaft 360 to the proximal tip 340. In this example, the torque shaft 360 may be configured as a torque shaft segment or sleeve as described above with reference to the introducer 200 or as further described below. The torque shaft segment 360 may include a coupling member 368A. The coupling member 368A may be configured as a substantially cylindrical tubular member. The coupling member 368A may include internal threads configured to engage external threads of the proximal tip as shown in FIG. 16. To that end, the diameter of the torque shaft 360 may increase in a distal to proximal direction at the coupling member 368A. This may form an annular space between the inner cannula 350 and the internal threads of the coupling member 368A in which the external threads of the proximal tip 340 may be received.

Figure 17:
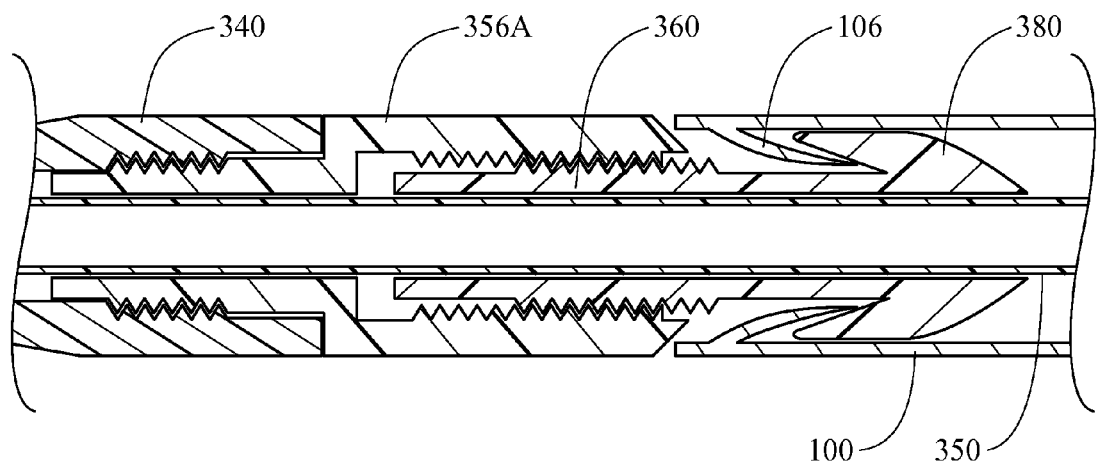
FIG. 17 is a longitudinal cross sectional view of a proximal portion of another example of an introducer.

FIG. 17 shows another example of the attachment of the torque shaft 360 to the proximal tip 340. In this example, the torque shaft 360 may be configured as a torque shaft segment or sleeve. A coupling member 356A may be attached to or integral with the proximal tip 340. Additionally, or alternatively, the coupling member 356A may be releasably attached to the torque shaft segment 360. A proximal portion of the coupling member 356A may include external threads configured to engage the internal threads 348 of the proximal tip 340 as described above. A distal portion of the coupling member 356A may be configured as a substantially cylindrical tubular member having internal threads configured to engage the external threads 368 of the proximal end of the torque shaft segment 360. To that end, the diameter of the distal portion of the coupling member 356A may be larger than the diameter of the proximal end of the torque shaft segment 360 so that the torque shaft segment may be received within the distal portion of the coupling member as shown in FIG. 17.

In one example, the coupling member 356A shown in FIG. 17 may include a distal extension portion. The distal extension portion may be configured as described above with reference to the distal extension portion 255 shown in FIG. 11. Additionally, or alternatively, the torque shaft segment 360 may include an insert segment. The insert segment may be configured as described above with reference to the insert segment 267 shown in FIG. 11. In this manner, the tapered distal face of the insert segment may form a smooth transition against which the apices of the stent 105 may slide during deployment of the stent, which may help to prevent catching or snagging the stent on the coupling member 356A during deployment of the stent.

Additionally, or alternatively, the introducer 300 may include a coupling member having any other suitable configuration. For example, the introducer 300 may include a coupling member having any suitable configuration such as, for example, any of those described above with reference to FIGS. 6-11.

Figure 18:
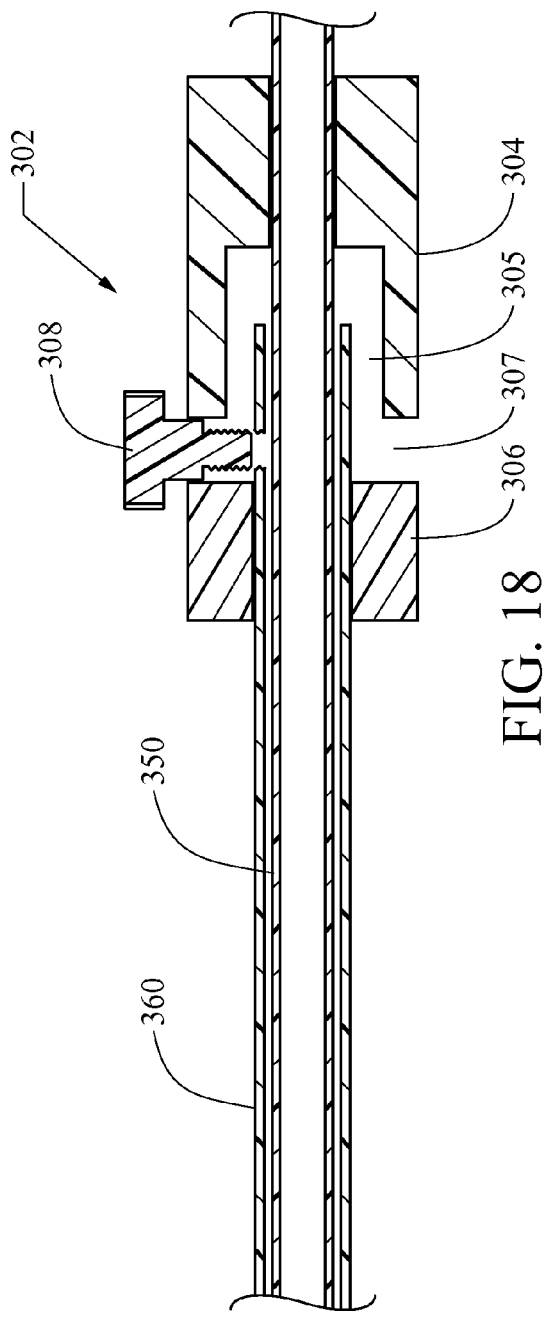
FIG. 18 is a partial longitudinal cross sectional view of a distal portion of one example of an introducer.

The introducer 300 may include a distal manipulation portion. The distal manipulation portion may be configured as a handle 302 as shown in FIGS. 13 and 18. The pusher catheter 320 and the pusher handle 308 are omitted from the embodiment shown in FIG. 18. The handle 302 may include the torque handle 306 and the cannula handle 304. The torque handle 306 may be configured as a tubular member having a substantially cylindrical shape. A lumen may extend longitudinally through the torque handle 306. The torque shaft 360 and the inner cannula 350 may be received within the lumen of the torque handle 306. The torque handle 306 may be attached to the torque shaft 360 as shown in FIG. 18. For example, the torque handle 306 may be fixedly attached to the torque shaft 360 so that longitudinal translation and/or rotation of the torque handle may be transmitted to the torque shaft. In other words, translating the torque handle 306 longitudinally with respect to the inner cannula 350 may cause the torque shaft 360 to translate longitudinally with respect to the inner cannula. Additionally, or alternatively, rotating the torque handle 306 about the longitudinal axis thereof relative to the inner cannula 350 may cause the torque shaft 360 to rotate about the longitudinal axis thereof relative to the inner cannula.

The cannula handle 304 may be configured as a tubular member having a substantially cylindrical shape. A lumen may extend longitudinally through the cannula handle 304. The inner cannula 350 may be received within the lumen of the cannula handle 304. Additionally, or alternatively, the torque shaft 360 may be at least partially received within the lumen of the cannula handle 304. The cannula handle 304 may be attached to the inner cannula 350 as shown in FIG. 18. For example, the cannula handle 304 may be fixedly attached to the inner cannula 350. A recess 305 may be formed in the proximal end of the cannula handle 304. The recess 305 may be configured as a generally cylindrical opening in the cannula handle 304. In other words, the recess 305 may be formed as a portion of the lumen of the cannula handle 304 having an increased diameter with respect to the remainder of the lumen of the cannula handle. The recess 305 may extend distally from the proximal end of the cannula handle 304 to receive the torque shaft 360. For example, the distal end of the torque shaft 360 may terminate within the recess 305. In this manner, the recess 305 may provide a space in which the torque shaft 360 may be free to rotate and/or translate relative to the inner cannula 350. To that end, the recess 305 may be sized and shaped to receive the torque shaft 360 and to allow relative movement of the torque shaft relative to the inner cannula 350 and the cannula handle 304. Alternatively, the distal end of the torque shaft 60 may terminate proximal of the recess 305. For example, the distal end of the torque shaft 360 may be substantially aligned with the distal end of the torque handle 306.

A longitudinal space 307 may be formed between the torque handle 306 and the cannula handle 302 as shown in FIGS. 13 and 18. The space 307 may enable the torque handle 306 to translate longitudinally relative to the cannula handle 304. For example, the torque handle 306 may translate distally relative to the inner cannula 350 such that the torque handle may move into the space 307 toward the cannula handle 304.

The handle 302 may include a locking mechanism such as a locking pin 308. The locking pin 308 may be positioned within the space 307 between the torque handle 306 and the cannula handle 304 to prevent translation and/or rotation of the torque handle relative to the cannula handle. To that end, the locking pin 308 may occupy substantially an entire longitudinal length of the space 307 to prevent the torque handle 306 from moving into the space 307 as described above. The locking pin 308 may be releasably attached to the torque handle 306, the cannula handle 304, and/or the torque shaft 360 by any attachment means. For example, the locking pin 308 may be threaded into a corresponding opening in the wall of the torque shaft 360 as shown in FIG. 18. Additionally, or alternatively, the locking pin may extend through the torque shaft 360 to engage the inner cannula 350. The locking pin 308 may be removed to enable rotation and/or translation of the torque shaft 360 relative to the inner cannula 350 as further described below. In other examples, the locking mechanism may be configured as any type of mechanism capable of fixing the position of the torque handle 306 relative to the cannula handle 304. For example, the locking mechanism may be configured as a known pin vise arrangement, a tab extending between the torque handle and the cannula handle, a push button configured to prevent movement of the torque handle relative to the cannula handle until depressed, or a sleeve temporarily coupling the torque handle to the cannula handle.

Returning to FIGS. 13-14, the deployment member 380 may include a proximal ring portion 382 and a distal transition portion 384. The proximal ring portion 382 may be configured as a tubular member having a substantially cylindrical shape. The distal transition portion 384 may be configured as a tubular member having a substantially conical shape. In other examples, the deployment member may include one or more projecting members such as tines or prongs configured to engage a portion of a stent (e.g., a strut or a bend of the stent). For example, the deployment member may include one or more stent engaging members as described above with reference to the introducer 200. The distal transition portion 384 may extend distally from the proximal ring portion 382 to form a tapered distal end of the deployment member 380 as further described below. In this manner, the deployment member 380 may extend proximally and outward away from the torque shaft 360. In other examples, the transition portion may be positioned proximal of the ring portion (i.e., the deployment member may extend distally and outward away from the torque shaft). A lumen may extend generally longitudinally within the deployment member 380 between a proximal end and a distal end of the deployment member. The torque shaft 360 may be received within the lumen of the deployment member 380 as shown in FIGS. 13-14. The deployment member 380 may be coupled to the torque shaft 360 as further described below. A proximal portion of the torque shaft 360 may extend proximally beyond the deployment member 380 to engage the proximal tip 340 as described above. A distal portion of the torque shaft 360 may extend distally beyond the deployment member 380 to the handle 302 of the introducer 300 as described above. Alternatively, the distal portion of the torque shaft may be omitted. In other words, the torque shaft may be configured as a torque shaft segment as described above.

The deployment member 380 may include a swivel 386 positioned radially between the transition portion 384 and the torque shaft 360. The deployment member 380 may be rotatably coupled to the torque shaft 360 via the swivel 386. To that end, the transition portion 384 of the deployment member 380 may be coupled to the swivel 386, and the swivel may be engaged with the torque shaft 360. The swivel 386 may be configured to enable the torque shaft 360 to rotate within the deployment member 380. Additionally, or alternatively, the swivel 386 may be configured to transmit longitudinal forces applied to the torque shaft 360 to the deployment member 380. In other words, the swivel 386 may be configured such that rotation of the torque shaft 360 about the longitudinal axis of the torque shaft relative to the inner cannula 350 does not cause the deployment member 380 to rotate relative to the inner cannula, but longitudinal translation of the torque shaft relative to the inner cannula does cause the deployment member 380 to translate longitudinally relative to the inner cannula. The swivel 386 may be configured as a tubular member having a substantially cylindrical shape. A lumen may extend longitudinally within the swivel 386. The torque shaft 360 may be received within the lumen of the swivel 386. An inner surface of the swivel 386 may be configured as a bearing surface to engage the torque shaft 360. In other words, the inner surface of the swivel 386 may be in abutting contact with an outer surface of the torque shaft 360.

The torque shaft 360 may include a pair of bands 363, one band positioned proximal to the swivel 386 and the other positioned distal to the swivel. The bands 363 may be configured as raised portions extending circumferentially around the outer surface of the torque shaft 360. The bands 363 may have an outer diameter that is larger than the diameter of the lumen of the swivel 386. The swivel 386 may be confined longitudinally on the torque shaft 360 between the bands 363. In this manner, the torque shaft 360 may be capable of rotating within the lumen of the swivel 386 without causing the deployment member 380 to rotate. Additionally, or alternatively, in this manner, longitudinal movement of the torque shaft 360 may be transmitted to the swivel 386 via the bands 363 to cause the deployment member 380 to move longitudinally. In other examples, the swivel 386 may be configured in any other manner that enables the torque shaft 360 and the deployment member 380 to interact as described above. For example, the swivel 386 may include a groove configured to receive a ridge formed in the outer surface of the torque shaft 360 or a ridge configured to be received within a groove formed in the outer surface of the torque shaft. Such configurations are contemplated by and within the scope of this disclosure.

The transition portion 384 of the deployment member 380 may provide a smooth taper between the relatively small outside diameter of the swivel 386 and the relatively larger outside diameter of the proximal ring portion 382. The smooth taper may reduce the potential for the introducer 300 to catch or snag on a deployed stent graft during withdrawal of the introducer through the stent graft as further described below. The proximal ring portion 382 of the deployment member 380 may be sized and shaped to engage a stent that may be loaded into the introducer as further described below.

Figure 19:
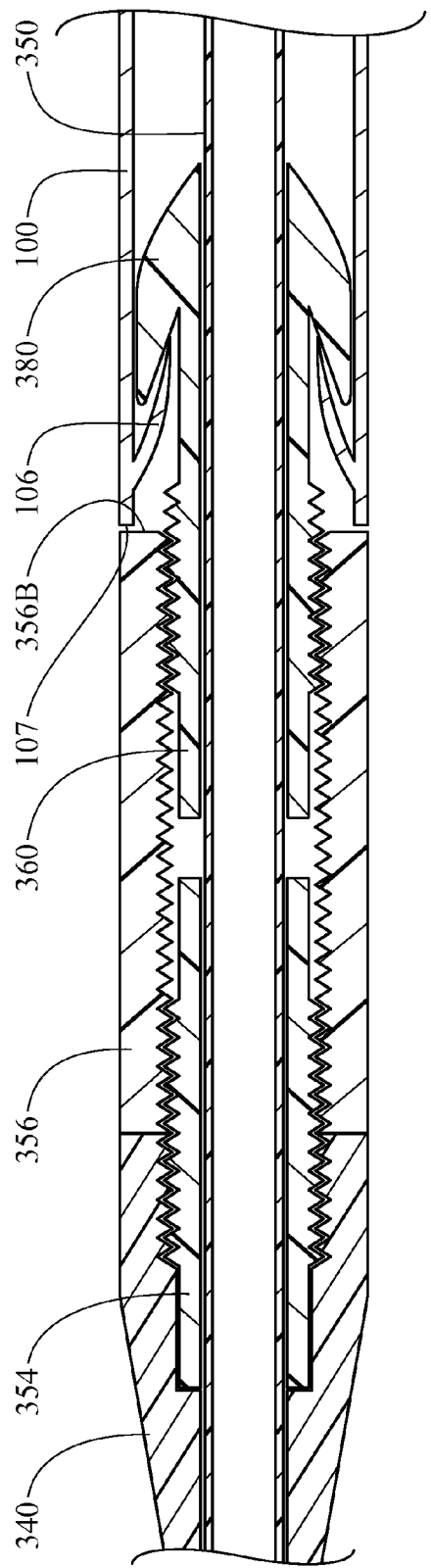
FIG. 19 is a partial longitudinal cross sectional view of a proximal portion of another example of an introducer.

In other examples, the deployment member 380 may be fixedly attached to the torque shaft 360. For example, the deployment member 380 may be fixedly attached to the torque shaft segment 360 as shown in FIGS. 16-17 and 19. To that end, the distal transition portion 384 of the deployment member 380 may include internal threads. The torque shaft segment 360 may include external threads positioned near a distal end of the torque shaft segment. The internal threads of the distal transition portion 384 of the deployment member 380 may engage with the external threads of the torque shaft segment 360 to attach the torque shaft and the deployment member to one another. Additionally, or alternatively, the deployment member 380 may be attached to the torque shaft 360 in any suitable manner. For example, the deployment member may be configured as a plurality of stent engagement members extending from the sleeve as described above with reference to the introducer 200 (e.g., as described in reference to any of FIGS. 3-12). In other examples, the deployment member 380 may be attached to the torque shaft 360 by bonding or welding, with adhesives, or by interference or friction fit. In other examples, the torque shaft segment 360 and the deployment member 380 may be formed as a unitary structure.

FIG. 19 shows another embodiment of the introducer 300. In this embodiment, the torque shaft 360 may be configured as a torque shaft segment. In other words, the torque shaft segment 360 may have a relatively short length (e.g., shorter than the length of the stent graft 100). The distal end of the torque shaft segment 360 may be positioned near the deployment member 380. In other words, the torque shaft segment 60a may not extend distally beyond the deployment member 380 and to the distal end of the introducer 300. In this embodiment, the torque shaft handle 306 may be omitted. The torque shaft segment 360 may be unattached to the handle 302 of the introducer 300. The deployment member 380 may be fixedly attached to the torque shaft segment 360, and the torque shaft segment may be configured to move longitudinally and/or rotationally relative to the inner cannula 350.

A threaded insert 354 may be attached to the proximal end of the inner cannula 350. For example, the threaded insert 354 may be fixedly attached (e.g., bonded or welded) to the inner cannula 350. The threaded insert 354 may include external threads configured to engage internal threads of the proximal tip 340 to couple the inner cannula 350 to the proximal tip. A coupling member 356 may be attached to the inner cannula 350 near the proximal end of the inner cannula. The coupling member 356 may form the distal end of the proximal tip 340 as described above with reference to the proximal tip 240 of the introducer 200. The coupling member 356 may be configured as a substantially cylindrical tubular member having internal threads. The coupling member 256 may be threadably engaged with the threaded insert 354 as shown in FIG. 19. In other examples, the inner cannula 350 may include a threaded portion to engage the internal threads of the proximal tip 340 and the internal threads of the coupling member 356. In other words, the inner cannula 350 may include a threaded portion such that the threaded insert 354 may be omitted. In still other examples, the proximal tip 340 may include a threaded portion having external threads, and the internal threads of the coupling member 356 may engage the external threads of the proximal tip. In one example, the coupling member 356 may be fixedly attached (e.g., bonded or welded) to the threaded insert. Additionally, or alternatively, the coupling member 356 may be fixedly attached directly to the inner cannula 350 and/or the proximal tip 340. The coupling member 356 may extend distally to engage the torque shaft segment 360. The proximal end of the torque shaft segment 360 may include external threads configured to engage the internal threads of the coupling member 356.

The engagement between the deployment member 380 and the projections 106 of the stent graft 100 may inhibit rotational movement of the torque shaft segment 360 relative to the stent graft. In other words, the deployment member 380 and the stent graft 100 may be frictionally engaged with one another such that rotational movement of the deployment member relative to the stent graft is inhibited. Rotation of the inner cannula 350 relative to the stent graft 100 may cause a corresponding rotation of the coupling member 356 relative to the torque shaft segment 360. Such rotation may cause the torque shaft segment 360 to disengage from the coupling member 356 to release the projections 106 of the stent graft 100.

A trigger wire (not shown) may be engaged with the deployment member 380, the torque shaft segment 360, the coupling member 356, the inner cannula 350, and/or the proximal tip 340. For example, the trigger wire may engage the torque shaft segment 360 and the coupling member 356. The trigger wire may prevent rotation of the coupling member 356 relative to the torque shaft segment 360. In other words, rotation of the inner cannula 350 with the trigger wire in place may cause a corresponding rotation of the torque shaft segment 360. Such rotation may cause rotation of the stent graft 100, which may be frictionally engaged with the deployment member 380 as described above. This may enable rotation of the stent graft 100 within the body vessel prior to complete deployment of the stent graft. Once the stent graft 100 is positioned as desired, the trigger wire may be removed so that further rotation of the inner cannula 350 may cause rotation of the coupling member 356 relative to the torque shaft segment 360. Additionally, or alternatively, the trigger wire may be threaded through a distal retention point of the stent graft 100 to aid in retaining the stent graft in place during release of the projections 106.

Returning to FIGS. 13-14, the pusher catheter 320 may be configured as an elongate tubular member having a substantially cylindrical shape. A lumen may extend generally longitudinally within the pusher catheter 320 between a proximal end and a distal end of the pusher catheter. A proximal end of the pusher catheter 320 may be positioned near the distal end 104 of the stent graft 100. The distal end 104 of the stent graft 100 may be releasably attached to the pusher catheter 320 to maintain tension on the stent graft as further described below. The distal end of the pusher catheter 320 may be attached to the pusher handle 308 such that manipulation of the pusher handle may cause the pusher catheter to rotate and/or translate longitudinally with respect to the inner cannula 350 and/or the torque shaft 360. The pusher handle 308 may include a locking member (e.g., a pin vice or locking pin), which may prevent translation and/or rotation of the pusher handle and the pusher catheter 320 relative to the inner cannula 350. The locking member may be released to enable rotation of the inner cannula 350 relative to the pusher catheter 320 to release the projections 106 of the stent graft 100 as described herein.

The sheath 330 of the introducer 300 may be configured as an elongate tubular member having a substantially cylindrical shape. A lumen may extend generally longitudinally within the sheath 330 between a proximal end and a distal end of the sheath. The proximal end of the sheath 330 may be configured to receive at least a portion of the proximal tip 340. For example, the proximal end of the sheath may be configured to receive at least a portion of the base portion 342 of the proximal tip 340 as shown in FIG. 14. To that end, the lumen of the sheath 330 may be sized to slide over the base portion 342 of the proximal tip 340 as further described below. The inner cannula 350, the torque shaft 360, and the deployment member 380 may be received within the lumen of the sheath 330. The distal end of the sheath may be attached to the sheath handle 332 such that manipulation of the sheath handle may cause the sheath to translate longitudinally with respect to the inner cannula 350 and/or the torque shaft 360.

FIG. 14 depicts the introducer 300 in a loaded configuration. In the loaded configuration, the stent graft 100 may be loaded in the introducer 300 for intraluminal deployment within the patient's body. The stent graft 100 may be in a reduced diameter, delivery configuration when the stent graft is loaded in the introducer 300. Additionally, or alternatively, the projections 106 of the stent graft 100 may be everted as shown in FIG. 14. When everted, the projections 106 may be folded over the proximal end 107 of the stent graft 100 such that the projections extend distally within the lumen 102 of the stent graft. In other words, the projections 106 may extend from the proximal end 107 of the stent graft 100 and external to the lumen 102 of the stent graft in the neutral configuration. The projections 106 and/or the proximal end 107 of the stent graft 100 may be rolled or folded inward toward the lumen 102 of the stent graft to move the projections from the neutral position external to the stent graft to the everted position within the lumen of the stent graft. Upon deployment of the stent graft 100, the projections 106 may return to the neutral configuration as shown in FIG. 1.

As shown in FIG. 14, the inner cannula 350, the torque shaft 360, and the deployment member 380 may be received within the lumen 102 of the stent graft 100. The deployment member 380 may engage the everted projections 106 of the stent graft 100, as further described below, to retain the proximal end 107 of the stent graft in a compressed configuration.

Additionally, or alternatively, the stent graft 100 may be engaged by the sheath 330 to retain the stent graft in the delivery configuration. For example, the graft body 101 of the stent graft 100 may be in contact with an inner surface of the sheath 330. The sheath 330 may oppose the radial expansion force of the stent graft 100 to retain the stent graft in the compressed delivery configuration.

The deployment member 380 may engage the stent graft 100 to retain at least a portion of the stent graft in a compressed configuration. For example, the deployment member 380 may engage the projections 106 of the stent graft 100 to retain the proximal end 107 of the stent graft in the compressed configuration. The proximal end of the deployment member 380 may be positioned radially between the projections 106 and an inner surface of the stent graft 100 as shown in FIG. 14. The proximal end 107 of the stent graft 100 may be in abutting contact with the distal facing surface 343 of the proximal tip 340. In this manner, at least a portion of the stent graft 100 may be confined longitudinally between the proximal tip 340 and the deployment member 380 to prevent the stent graft from translating longitudinally with respect to the introducer 300. In other words, the distal facing surface 343 of the proximal tip 340 may prevent the stent graft 100 from moving proximally with respect to the inner cannula 350 and/or the proximal tip 340, and the deployment member 380 may prevent the stent graft from moving distally with respect to the inner cannula and/or the proximal tip.

The stent graft 100 may be prevented from translating longitudinally by any suitable means. This may aid in retaining the projections 106 in engagement with the deployment member 380. In one example, the proximal end 107 of the stent graft 100 may be in abutting contact with a distal facing surface 356B of the coupling member 356 as shown in FIG. 19. The distal facing surface 356B of the coupling member 356 may be a blunt surface configured to engage the stent graft 100. For example, the distal facing surface 356B may form the distal facing surface of the proximal tip as described above with respect to the distal facing surface 343. In this manner, at least a portion of the stent graft 100 may be confined longitudinally between the coupling member 356 and the deployment member 380 to prevent the stent graft from translating longitudinally with respect to the introducer 300. The distal end 104 of the stent graft may be unattached to the introducer 300. Accordingly, the pusher catheter 320 and the pusher handle 306 may be omitted.

In another example, the proximal end 107 of the stent graft 100 may not be in abutting contact with a distal facing surface. For example, the proximal end 107 of the stent graft 100 may be spaced from the coupling member 356 as shown in FIG. 16. The distal end 104 of the stent graft 100 may be releasably attached to the introducer 300 to maintain longitudinal tension on the stent graft to prevent the stent graft from translating longitudinally with respect to the introducer. For example, the distal end 104 of the stent graft 100 may be releasably attached to the pusher catheter 320. The distal end 104 of the stent graft 100 may be releasably attached to the introducer 300 in any known manner. For example, a trigger wire may extend along a length of the introducer 300 to engage the distal end 104 of the stent graft 100 and the introducer (e.g., the pusher catheter 320) to releasably attach the stent graft to the introducer. The stent graft 100 may be prevented from translating longitudinally in a proximal direction relative to the introducer 300 (e.g., relative to the inner cannula 350 and/or the proximal tip 340) by engagement between the stent graft and the pusher catheter 320. The stent graft 100 may be prevented from translating longitudinally in a distal direction relative to the introducer 300 by engagement between the stent graft and the deployment member 380.

The proximal end 107 of the stent graft 100 may be retained in the compressed configuration (even after retraction of the sheath 330 as further described below) by the deployment member 380. In other words, the stent graft 100 may be retained in a partially expanded configuration after retraction of the sheath 330 by the deployment member 380. For example, the projections 106 may be positioned in the annular space between the deployment member 380 and the torque shaft 360 as shown in FIG. 14. In this manner, the proximal end 107 of the stent graft 100 may be prevented from expanding from the compressed configuration. Additionally, the projections 106 may be retained in the everted configuration by the deployment member 380. In other words, the projections 106 of the stent graft 100 may be retained within the annular space between the deployment member 380 and the torque shaft 360 such that the projections may be unable to revert to a position external to the lumen 102 of the stent graft 100 as shown in FIG. 1. It should be noted that the deployment member 380 may be configured to retain the proximal end 107 of the stent graft 100 in the compressed configuration without any trigger wires. In other words, it may be unnecessary to engage the proximal end 107 of the stent graft 100 with a trigger wire to retain the proximal end 107 in the compressed configuration. Because such trigger wires may be unnecessary, the introducer 300 may be less complex to operate and/or may have a lower profile as compared to traditional introducers.

Figure 20:
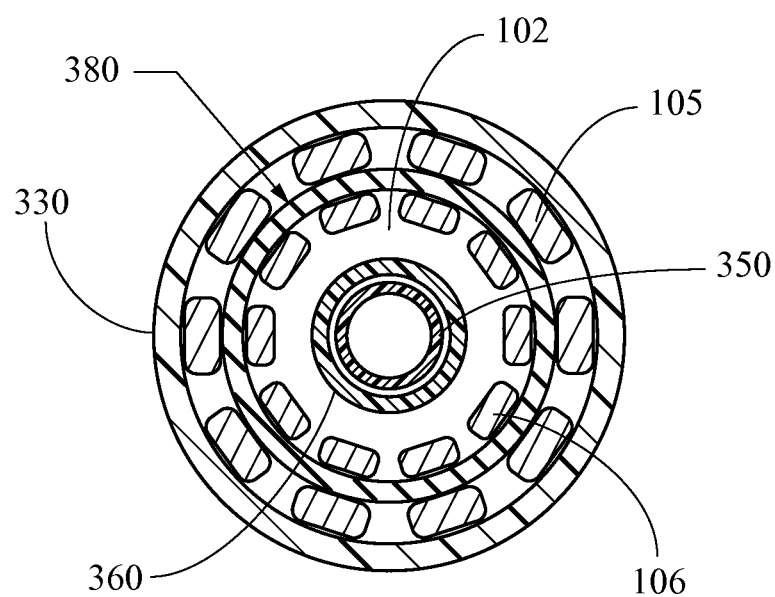
FIG. 20 is a transverse cross sectional view of the introducer system of FIG. 14 taken along line A-A.

FIG. 20 is a transverse cross sectional view of the introducer 300 and the stent graft 100 taken along line A-A of FIG. 14. As shown in FIG. 20, the inner cannula 350 may be received within the lumen of the torque shaft 360. The inner cannula 350 and the torque shaft 360 may be received within the lumen of the deployment member 380. The inner cannula 350, the torque shaft 360, and the deployment member 380 may be coaxial. The inner cannula 350, the torque shaft 360, and the deployment member 380 may be received within the lumen 102 of the stent graft 100. The deployment member 380 may be positioned between the projections 106 and the stent 105 of the stent graft 100 to retain the proximal end 107 of the stent graft in the compressed configuration. The stent graft 100 may be received within the sheath 330 to retain the stent graft in the delivery configuration.

FIGS. 14 and 21-23 illustrate one example of a method for deploying a stent graft. The stent graft 100 may be loaded into the introducer 300, as shown in FIG. 14, by any means. For example, with the stent graft 100 in the expanded configuration, the proximal tip 340 may be inserted into the lumen 102 of the stent graft from the distal end 104 of the stent graft. The introducer 300 may be advanced proximally within the lumen 102 of the stent graft 100 until the proximal tip 340 exits the proximal end 107 of the lumen 102. The sheath 330 may be retracted distally relative to the inner cannula 350. The sheath 330 may be retracted a sufficient distance to allow the stent graft 100 to be compressed around the inner cannula 350 (i.e., to remove the sheath from the lumen 102 of the stent graft). The torque shaft 360 may be unlocked from the proximal tip 340 and/or retracted distally relative to the inner cannula 350 such that the proximal end of the deployment member 380 may be positioned distal to the projections 106 of the stent graft 100.

The stent graft 100 may be compressed (e.g., into the delivery configuration) around the inner cannula 350 and/or the torque shaft 360. The stent graft 100 may be compressed into the delivery configuration by any means (e.g., a funnel or a radial compression tool). In one example, the stent graft 100 may be compressed in a hollow mandrel disposed around the exterior of the stent graft. The projections 106 of the stent graft 100 may be everted such that the projections may be brought into abutting contact with the torque shaft 360. To that end, the mandrel may include a series of holes positioned around the circumference of the mandrel. Pins may be inserted into the holes to depress the projections 106 of the stent graft 100 toward the inner cannula 350. The torque shaft 360 may be advanced proximally relative to the inner cannula 350 so that the deployment member 380 may engage the everted projections 106 of the stent graft 100. The torque shaft 360 may be advanced proximally by threading the proximal end of the torque shaft 360 into the proximal tip 340 as described above. Advancing the torque shaft 360 proximally may bring the proximal end 107 of the stent graft 100 into abutting contact with the distal facing surface 343 of the proximal tip 340. The torque shaft 360 may be locked to the proximal tip 340 as described above. For example, the torque shaft 360 may be rotated to thread the proximal end of the torque shaft into the proximal tip 340. The sheath 330 may be advanced proximally relative to the inner cannula 350 to engage the stent graft 100. The mandrel may be removed as the sheath 330 is advanced. The sheath 330 may be advanced until the proximal end of the sheath engages the proximal tip 340 as described above.

The introducer 300 and the stent graft 100 in the loaded configuration may be navigated to a desired position within a patient's body using known techniques. For example, the introducer may be navigated to a position within a patient's aorta. A guide wire may be introduced into the femoral artery and advanced until the tip of the guide wire is above the region into which the stent graft 100 is to be deployed. The introducer 300 may be advanced over the guide wire until the stent graft 100 is in the desired position. An oscillating, rotating action may be used to aid in advancing the introducer 300 over the guide wire, particularly in tortuous anatomy.

Figure 21:
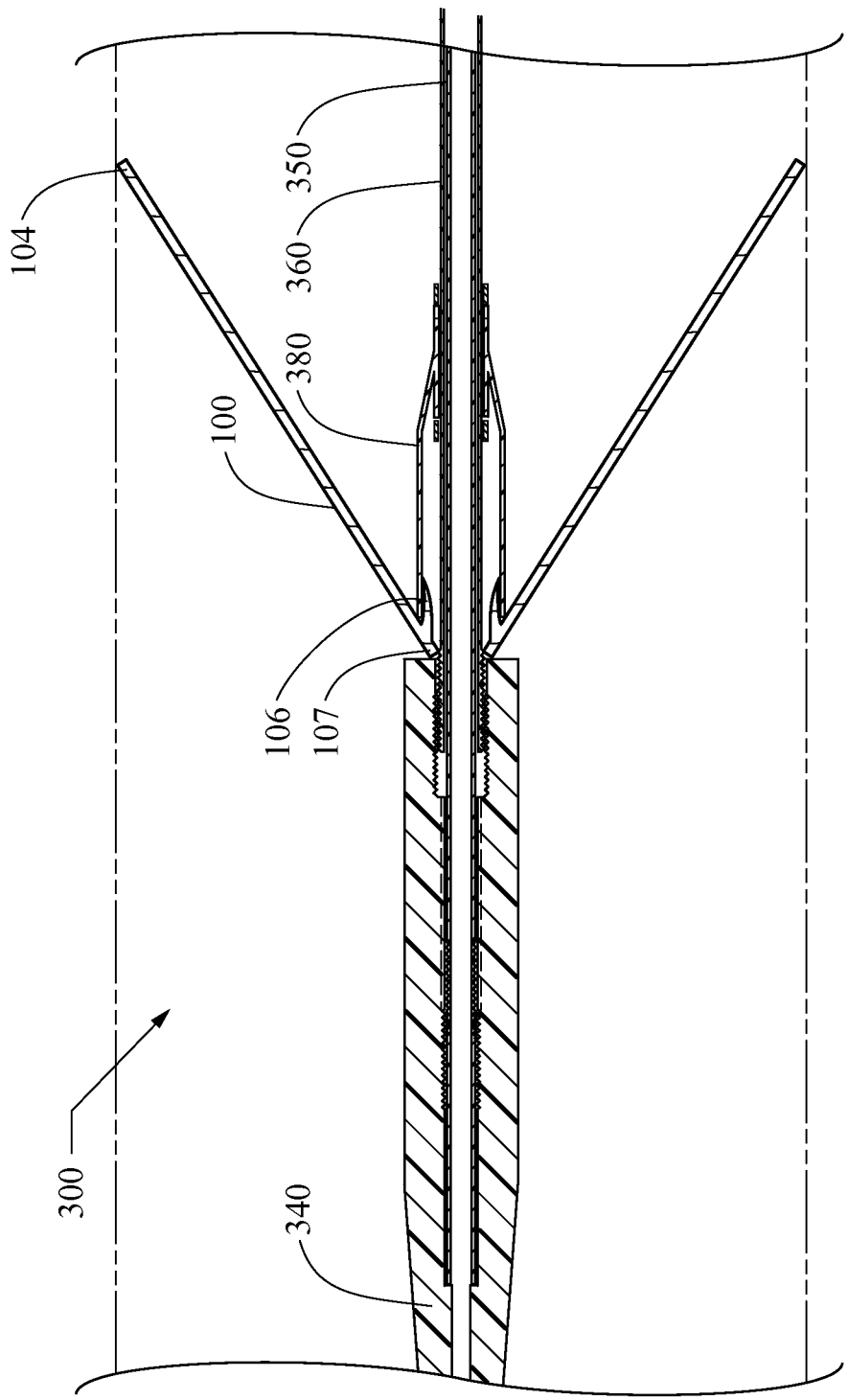
FIG. 21 is a longitudinal cross sectional view of the proximal portion of the introducer of FIG. 14 with a sheath retracted to partially deploy the stent graft.

When the introducer 300 is in the desired position for deployment of the stent graft 100, the sheath 330 may be retracted to expose the stent graft. The sheath 330 may be retracted, for example, by manipulating the sheath handle 332 to move the sheath distally relative to the inner cannula 350. Retracting the sheath 330 may enable partial deployment of the stent graft 100. For example, when the sheath 330 is no longer positioned to oppose the radial expansion force of the stent graft 100, the distal end 104 of the stent graft may expand from the delivery configuration as shown in FIG. 21. The proximal end 107 of the stent graft 100 may be retained in the compressed configuration by the deployment member 380 as described above. In other words, the stent graft 100 may be allowed to expand to the partially expanded configuration by retraction of the sheath 330. Such partial deployment of the stent graft 100 may enable a physician to reposition the stent graft prior to complete deployment of the stent graft. The position of the stent graft 100 within the body vessel may be viewed during deployment using fluoroscopy or other visualization technique. Because the proximal end 107 of the stent graft 100 may be retained by the deployment member 380, the projections 106 of the stent graft may not engage the wall of the body vessel. The partially deployed stent graft 100 may not be fixed in place relative to the body vessel, thus allowing the physician to reposition the stent graft prior to complete deployment of the stent graft.

When the stent graft 100 has been repositioned as desired, the torque shaft 360 may be unlocked and/or detached from the proximal tip 340. The torque shaft 360 may be unlocked, for example, by manipulating the handle 302 of the introducer to rotate the torque shaft about its longitudinal axis relative to the inner cannula 350. Such rotation may cause the proximal end of the torque shaft 360 to unthread from the proximal tip 340. During such rotation, the torque shaft 360 may rotate within the swivel 386 such that the deployment member 380 is not caused to rotate. The deployment member 380 may be retracted distally to disengage from the proximal end 107 of the stent graft 100. The deployment member 380 may be retracted, for example, by longitudinal movement of the torque shaft 360 relative to the inner cannula 350 caused by unthreading the torque shaft from the proximal tip 340. In another example, the deployment member 380 may be retracted by manipulating the handle of the introducer 300 to move the torque shaft 360 distally relative to the inner cannula 350. Such retraction of the torque shaft 360 may cause the deployment member 380 to move distally relative to the inner cannula 350 and the stent graft 100. In yet another example, the deployment member 380 may be retracted by rotation of the inner cannula 350 relative to the torque shaft segment 360 as described above in reference to FIG. 19. Such rotation may cause the torque shaft segment 360 and the deployment member 380 to move longitudinally away from the coupling member 356.

Figure 22:
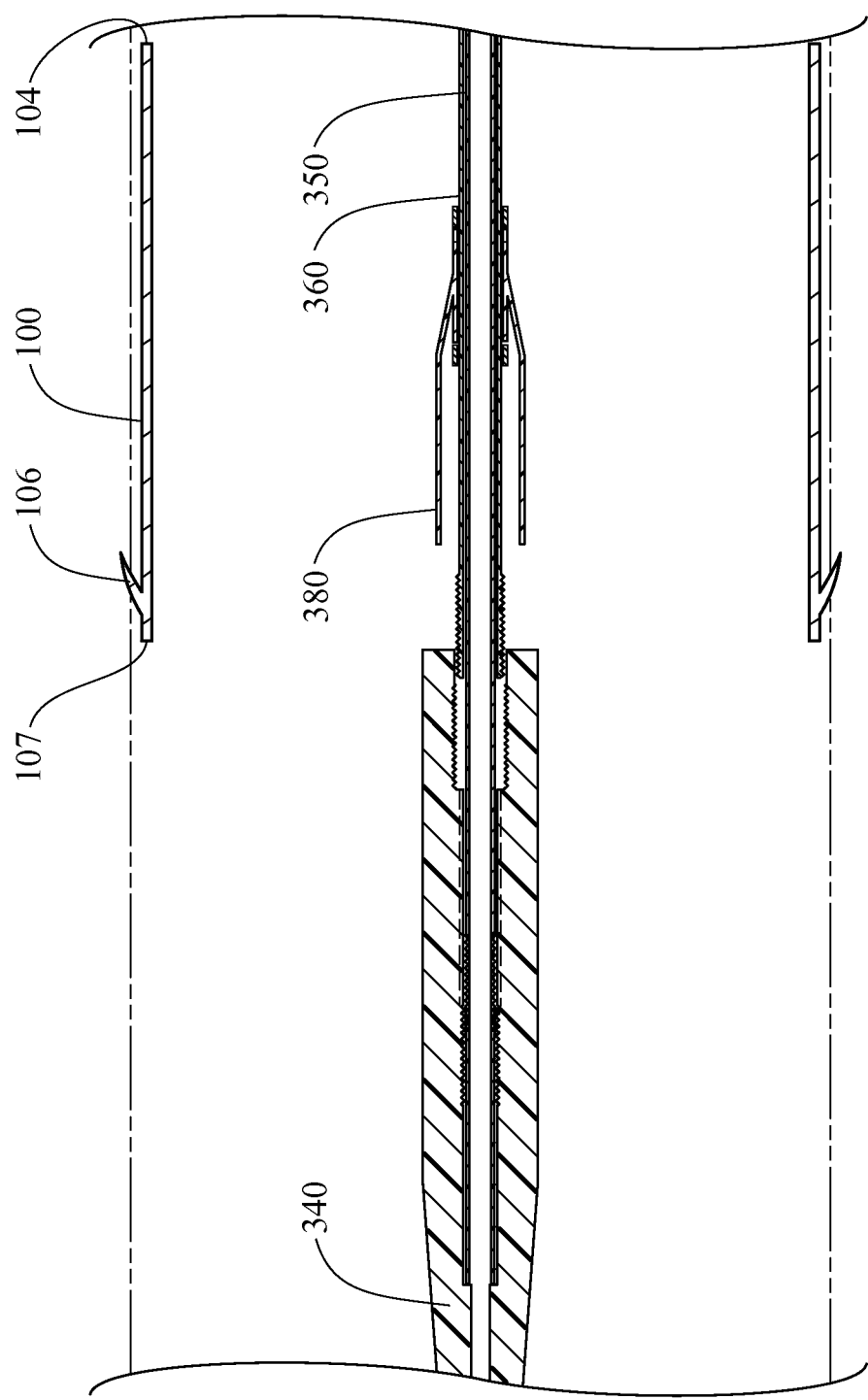
FIG. 22 is a longitudinal cross sectional view of the proximal portion of the introducer of FIG. 14 with the stent graft fully deployed.

In any of these examples, such movement of the deployment member 380 relative to the inner cannula 250 and/or the proximal tip 340 may enable the complete deployment of the stent graft 100. For example, when the deployment member 380 is no longer positioned to engage the projections 106 of the stent graft 100, the projections may revert to a position external to the lumen 102 of the stent graft, and the proximal end 107 of the stent graft may expand to the deployed configuration as shown in FIG. 22. Upon complete deployment, the projections 106 of the stent graft 100 may engage the wall of the body vessel to fix the stent graft in place relative to the body vessel. It should be noted that complete deployment of the stent graft 100 may be accomplished without the use or manipulation of any trigger wires.

Figure 23:
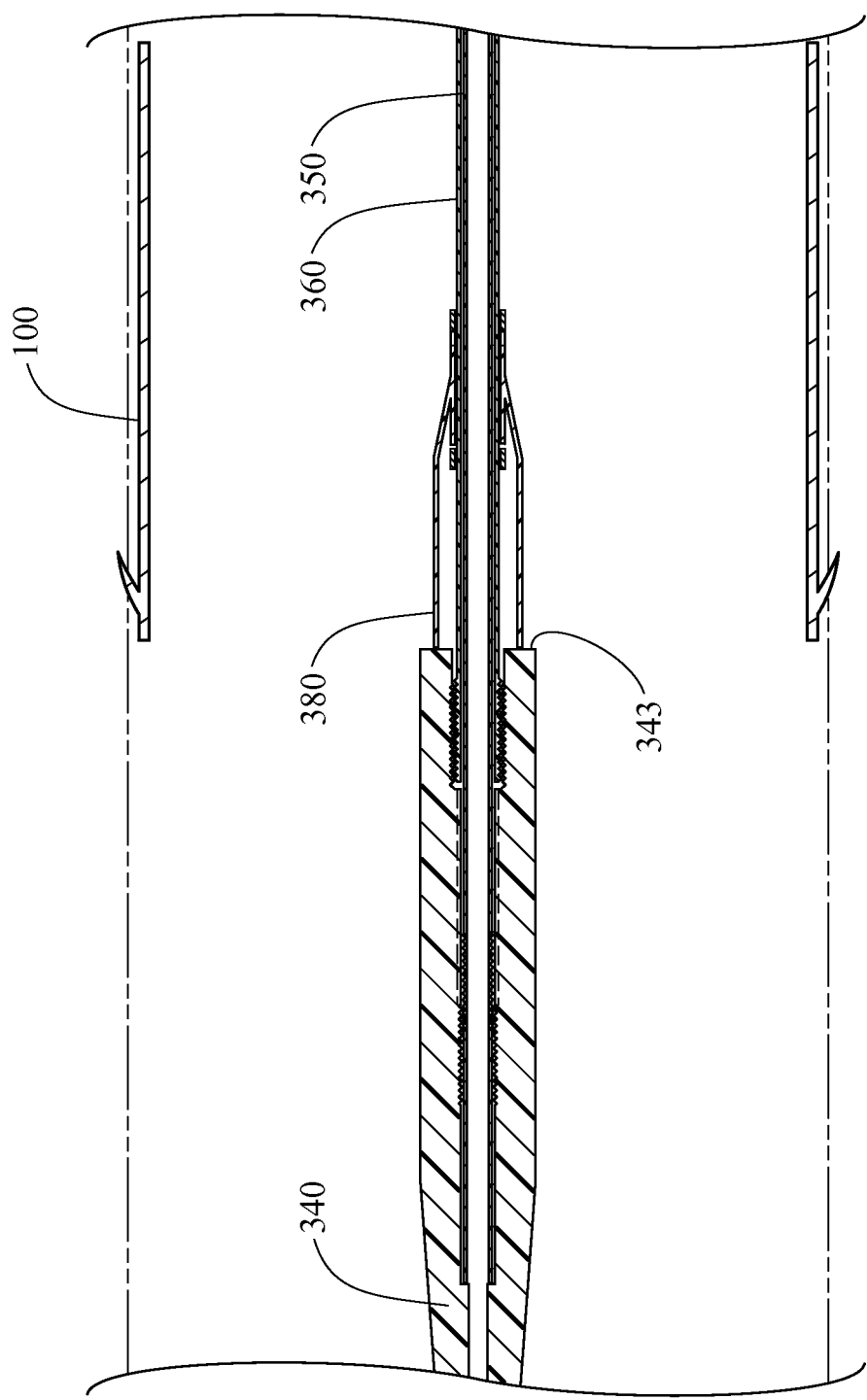
FIG. 23 is a longitudinal cross sectional view of the proximal portion of the introducer of FIG. 14 with the introducer in the withdrawal configuration.

Following complete deployment of the stent graft 100, the introducer 300 may be manipulated into a withdrawal configuration. In the withdrawal configuration, the deployment member 380 may be in a withdrawal position. In the withdrawal position, the proximal end of the deployment member 380 may be in abutting contact with the distal facing surface 343 of the proximal tip 340 as shown in FIG. 23. The deployment member 380 may be moved to the withdrawal configuration by threading the torque shaft 360 further into the proximal tip 340. If the torque shaft 360 was detached from the proximal tip 340 to disengage the stent graft 100, the torque shaft 360 may first be reattached to the proximal tip 340. The torque shaft 360 may be advanced proximally relative to the inner cannula 350, for example, by manipulating the handle 302 of the introducer 300. The torque shaft 360 may be advanced until the proximal end of the torque shaft engages the proximal tip 340. The torque shaft 360 may be attached, or locked, to the proximal tip 340, for example, by manipulating the handle 302 of the introducer 300 to rotate the torque shaft about its longitudinal axis relative to the inner cannula 350. Such rotation may cause the proximal end of the torque shaft 360 to thread into the proximal tip 340. The torque shaft 360 may be rotated (and may be further threaded into the proximal tip 340) until the proximal end of the deployment member 380 is in abutting contact with the distal facing surface 343 of the proximal tip 340 as shown in FIG. 23.

With the deployment member 380 in the withdrawal position, the introducer 300 may be withdrawn from the patient's body. While holding the sheath 330 in a fixed position, the inner cannula 350, the proximal tip 340, the torque shaft 360, and the deployment member 380 may be retracted distally with respect to the sheath 330 until the sheath engages the proximal tip 340. The tapered distal end defined by the conical shape of the transition portion 384 of the deployment member 380 may provide a smooth taper from the outside diameter of the torque shaft 360 to the outside diameter of the proximal ring portion 382 of the deployment member. The smooth taper may reduce the potential for the introducer 300 to catch or snag on the deployed stent graft 100 as the introducer is withdrawn through the lumen 102 of the stent graft 100. The introducer 300 may be further withdrawn until the proximal tip 340 exits the patient's body.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. An endoluminal prosthesis introducer comprising:
   a distal end, a proximal end and a proximal tip having a tip lumen;
   a rotatable innermost cannula having comprising a lumen, a proximal end, a proximal end portion, and a distal end, the rotatable innermost cannula extending from at least just proximal the distal end of the introducer and at least partially through the proximal tip lumen;
   the proximal tip disposed at the proximal end of the innermost cannula and comprising a distal end; and
   a retaining member comprising an engaging member extending radially outward, the retaining member disposed directly over and about the proximal end portion of the innermost cannula, whereby, in response to rotation of the innermost cannula with respect to the retaining member, the proximal tip is longitudinally movable relative to the engaging member between a retaining configuration and a releasing configuration, wherein the proximal tip and the engaging member are spaced from one another by a greater longitudinal distance in the releasing configuration than in the retaining configuration.

2. The introducer of claim 1, wherein the retaining member comprises a sleeve disposed about the innermost cannula, and the engaging member comprises a plurality of engaging members disposed circumferentially about the sleeve and extending radially from the sleeve.

3. The introducer of claim 1, wherein the retaining member comprises a sleeve disposed about the innermost cannula, the engaging member extends radially from the sleeve, and the sleeve is engageable with the proximal tip.

4. The introducer of claim 3, wherein the sleeve of the retaining member comprises an attachment mechanism positioned proximal of the engaging member, the distal end of the proximal tip comprises a coupling member comprising an attachment mechanism, and the attachment mechanism of the sleeve is engageable with the attachment mechanism of the coupling member to couple the retaining member to the proximal tip.

5. The introducer of claim 3, wherein the sleeve of the retaining member comprises an attachment mechanism positioned proximal of the engaging member and comprising a threaded segment of the sleeve.

6. The introducer of claim 1, wherein the distal end of the proximal tip comprises a blunt, distal facing surface.

7. The introducer of claim 1, wherein the distal end of the proximal tip comprises a curved distal facing surface, and the engaging member comprises a curved proximal edge dimensioned to engage the curved distal facing surface of the proximal tip.

8. The introducer of claim 1, wherein the retaining member comprises a sleeve disposed about the innermost cannula, the engaging member comprises a fin extending longitudinally along and outward away from the sleeve and comprising a projection extending proximally from a proximal edge of the fin, and the retaining member comprises a notch positioned radially between the projection and the sleeve.

9. The introducer of claim 8, wherein the fin comprises a tapered distal edge.

10. The introducer of claim 1, wherein the retaining member comprises a sleeve disposed about the innermost cannula, the sleeve comprises an insert segment disposed proximal of the engaging member and comprising a tapered distal face, and, in response to longitudinal movement of the proximal tip relative to the engaging member, the insert segment is movable between a first configuration in which the tapered distal face is disposed within the proximal tip and a second configuration in which at least a portion of the tapered distal face is disposed outside of the proximal tip.

11. The introducer of claim 1, wherein the retaining member comprises a sleeve disposed about the innermost cannula and comprising a threaded segment engageable with the proximal tip, a proximal sleeve extension extending proximally beyond the threaded segment, and a crown member disposed at a proximal end of the proximal sleeve extension, the distal end of the proximal tip comprises a chamber and a tubular segment extending distally from the chamber and comprising a lumen extending longitudinally within the tubular segment, the proximal sleeve extension is disposed within the lumen of the tubular segment, and the crown member is disposed within the chamber and comprises a larger diameter than the lumen of the tubular segment.

12. The introducer of claim 11, wherein the proximal tip comprises a resilient member disposed within the chamber and proximal of the crown member of the retaining member.

13. A system comprising:
    an introducer and an endoluminal prosthesis loaded on the introducer;
    the prosthesis comprising a stent end engaged by the introducer and retained in a compressed configuration;
    the introducer comprising:
       a rotatable innermost cannula comprising a proximal end, a proximal end portion, and a distal end, the rotatable innermost cannula extending from at least just proximal the distal end of the introducer and at least partially through the proximal tip lumen;
       the proximal tip disposed at the proximal end of the innermost cannula and comprising a distal end; and
       a retaining member disposed directly over and about the proximal end portion of the innermost cannula and comprising a sleeve and an engaging member extending radially from the sleeve and engaged with the stent end in the compressed configuration, whereby the stent end is retained against the distal end of the proximal tip, and, in response to rotation of the innermost cannula with respect to the prosthesis and the retaining member, the proximal tip is longitudinally movable relative to the engaging member from a retaining configuration to a releasing configuration, and the stent end is releasable from engagement with the engaging member.

14. The system of claim 13, wherein the stent end comprises a plurality of apices, the engaging member comprises a plurality of engaging members disposed circumferentially about the sleeve of the retaining member, and each engaging.

15. The system of claim 14, wherein each of the plurality of apices is engaged by a corresponding engaging member to retain the stent end in the compressed configuration.

16. The system of claim 14, wherein at least one apex comprises an eyelet disposed at a proximal end of the apex, and the eyelet is engaged by a corresponding engaging member.

17. The system of claim 13, wherein the engaging member comprises a plurality of engaging members disposed circumferentially about the sleeve and extending radially from the sleeve, each of the engaging members comprises a tapered distal edge, a distal portion of the sleeve comprises a tapered outer surface, and the tapered distal edges of the engaging members and the tapered outer surface of the sleeve cooperatively form a frustoconical outer surface of the retaining member.

18. The system of claim 13, wherein the engaging member comprises a tubular member comprising a proximal ring portion, a tapered distal transition portion, and a lumen extending longitudinally within the engaging member, and the sleeve of the retaining member is disposed within the lumen of the engaging member.

19. The system of claim 13, wherein the stent end comprises at least one projection extending distally from the stent end, the projection is movable between a neutral position and an everted position, and the engaging member engages the projection in the everted position to retain the stent end in the compressed configuration.

* * * * *